(12) United States Patent
Church et al.

(10) Patent No.: US 11,085,072 B2
(45) Date of Patent: Aug. 10, 2021

(54) METHODS OF GENERATING LIBRARIES OF NUCLEIC ACID SEQUENCES FOR DETECTION VIA FLUORESCENT IN SITU SEQUENCING

(71) Applicant: President and Fellows of Harvard College, Cambridge, MA (US)

(72) Inventors: George M. Church, Brookline, MA (US); Evan R. Daugharthy, Cambridge, MA (US); Richard C. Terry, Carlisle, MA (US); Benjamin W. Pruitt, Cambridge, MA (US); Brian M. Turczyk, Westford, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/285,292

(22) Filed: Feb. 26, 2019

(65) Prior Publication Data
US 2019/0177718 A1    Jun. 13, 2019

Related U.S. Application Data

(63) Continuation of application No. PCT/US2017/049633, filed on Aug. 31, 2017.
(Continued)

(51) Int. Cl.
*C12Q 1/6832* (2018.01)
*C12Q 1/6806* (2018.01)
(Continued)

(52) U.S. Cl.
CPC ....... *C12Q 1/6832* (2013.01); *C12N 15/1065* (2013.01); *C12N 15/1093* (2013.01);
(Continued)

(58) Field of Classification Search
CPC .. C12Q 1/6832; C12Q 1/6816; C12Q 1/6874; C12Q 1/6806; C12N 15/1065
See application file for complete search history.

(56) References Cited

U.S. PATENT DOCUMENTS

| 4,123,610 A | 10/1978 | Summerton et al. |
| 4,844,617 A | 7/1989 | Kelderman et al. |

(Continued)

FOREIGN PATENT DOCUMENTS

| EP | 2878671 A1 | 6/2015 |
| JP | 2012-170337 A | 9/2012 |

(Continued)

OTHER PUBLICATIONS

Zhou et al. (Experimental and Molecular Pathology, 2001,70:281-288) (Year: 2001).*

(Continued)

*Primary Examiner* — Jeremy C Flinders
(74) *Attorney, Agent, or Firm* — Banner & Witcoff, Ltd.

(57) ABSTRACT

The present disclosure provides a number of targeted nucleic acid FISSEQ library construction methods. Targeted FISSEQ can exhibit several benefits, such as enhanced sensitivity and/or shorter assay time in the detection, identification, quantification, and/or determining the nucleotide sequence of the target species, relative to "random" or "whole-omic" detection via FISSEQ.

18 Claims, 7 Drawing Sheets

Specification includes a Sequence Listing.

Related U.S. Application Data

(60) Provisional application No. 62/381,980, filed on Aug. 31, 2016.

(51) Int. Cl.
  *C12N 15/10* (2006.01)
  *C12Q 1/6816* (2018.01)
  *C12Q 1/6874* (2018.01)
  *C12Q 1/6844* (2018.01)
  *C12Q 1/6869* (2018.01)

(52) U.S. Cl.
  CPC ......... *C12Q 1/6806* (2013.01); *C12Q 1/6816* (2013.01); *C12Q 1/6844* (2013.01); *C12Q 1/6869* (2013.01); *C12Q 1/6874* (2013.01)

(56) References Cited

U.S. PATENT DOCUMENTS

| | | | |
|---|---|---|---|
| 4,886,741 A * | 12/1989 | Schwartz | C12Q 1/6832 435/5 |
| 4,981,985 A | 1/1991 | Kaplan et al. | |
| 5,151,189 A | 9/1992 | Hu et al. | |
| 5,563,056 A | 10/1996 | Swan et al. | |
| 5,594,235 A | 1/1997 | Lee | |
| 5,695,940 A | 12/1997 | Drmanac et al. | |
| 5,830,708 A | 11/1998 | Naughton | |
| 5,834,758 A | 11/1998 | Trulson et al. | |
| 5,871,921 A | 2/1999 | Landegren et al. | |
| 6,083,726 A | 7/2000 | Mills, Jr. et al. | |
| 6,306,597 B1 | 10/2001 | Macevicz | |
| 6,534,266 B1 | 3/2003 | Singer | |
| 6,586,176 B1 | 7/2003 | Trnovsky et al. | |
| 6,632,655 B1 | 10/2003 | Mehta et al. | |
| 7,255,994 B2 | 8/2007 | Lao | |
| 7,323,305 B2 | 1/2008 | Leamon et al. | |
| 7,427,479 B2 | 9/2008 | Karger et al. | |
| 7,473,767 B2 | 1/2009 | Dimitrov | |
| 7,745,129 B1 | 6/2010 | Schatz | |
| 7,906,285 B2 | 3/2011 | Drmanac | |
| 8,124,751 B2 | 2/2012 | Pierce et al. | |
| 8,268,554 B2 | 9/2012 | Schallmeiner | |
| 8,329,404 B2 | 12/2012 | McKernan et al. | |
| 8,460,865 B2 | 6/2013 | Chee et al. | |
| 8,501,459 B2 | 8/2013 | Chen et al. | |
| 8,551,710 B2 | 10/2013 | Bernitz et al. | |
| 9,201,063 B2 | 12/2015 | Sood et al. | |
| 9,217,151 B2 | 12/2015 | Yin et al. | |
| 10,138,509 B2 | 11/2018 | Church et al. | |
| 10,227,639 B2 | 3/2019 | Levner et al. | |
| 10,266,888 B2 | 4/2019 | Daugharthy et al. | |
| 10,267,808 B2 | 4/2019 | Cai | |
| 10,494,662 B2 | 12/2019 | Church et al. | |
| 10,494,667 B2 | 12/2019 | Chee | |
| 10,545,075 B2 | 1/2020 | Deisseroth et al. | |
| 2002/0015952 A1 | 2/2002 | Anderson et al. | |
| 2002/0155989 A1 | 10/2002 | Efimov et al. | |
| 2002/0172950 A1 | 11/2002 | Kenny et al. | |
| 2003/0148335 A1 | 8/2003 | Shen et al. | |
| 2004/0077014 A1 | 4/2004 | Becker | |
| 2004/0248144 A1 | 12/2004 | Mir | |
| 2004/0259190 A1 | 12/2004 | Naughton | |
| 2005/0106629 A1 | 5/2005 | McGrath et al. | |
| 2005/0147981 A1 | 7/2005 | Yamakawa et al. | |
| 2005/0191687 A1 | 9/2005 | Wang et al. | |
| 2005/0233318 A1 | 10/2005 | Chee et al. | |
| 2006/0024711 A1 | 2/2006 | Lapidus et al. | |
| 2006/0077536 A1 | 4/2006 | Bromage et al. | |
| 2006/0177833 A1 | 8/2006 | Brenner | |
| 2006/0183107 A1 | 8/2006 | Melkonyan et al. | |
| 2006/0228733 A1 | 10/2006 | Pierce et al. | |
| 2006/0234261 A1 | 10/2006 | Pierce et al. | |
| 2006/0248349 A1 | 11/2006 | Rathjen et al. | |
| 2006/0292611 A1 | 12/2006 | Berka et al. | |
| 2007/0020650 A1 | 1/2007 | Kahvejian | |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0206275 A1 | 9/2007 | Hemmer et al. |
| 2007/0231823 A1 | 10/2007 | McKernan et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0269068 A1 | 10/2008 | Church et al. |
| 2009/0005259 A1 | 1/2009 | Drmanac |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0223585 A1 | 9/2011 | Gullberg et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0252686 A1 | 10/2012 | Umbarger et al. |
| 2012/0330636 A1 | 12/2012 | Albou |
| 2013/0017229 A1 | 1/2013 | Mooney et al. |
| 2013/0245096 A1 | 9/2013 | Abitbol |
| 2014/0049632 A1 | 2/2014 | Hemmer |
| 2014/0087378 A1 | 3/2014 | Chatre et al. |
| 2014/0087427 A1 | 3/2014 | Bujnicki et al. |
| 2014/0200146 A1 | 7/2014 | Xie et al. |
| 2014/0220587 A1 | 8/2014 | Green, Jr. et al. |
| 2014/0270435 A1 | 9/2014 | Dunn |
| 2015/0133319 A1 | 5/2015 | Fu et al. |
| 2016/0024555 A1 | 1/2016 | Church et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2017/0176338 A1 | 6/2017 | Wu et al. |
| 2017/0212983 A1 | 7/2017 | Cai et al. |
| 2018/0010166 A1 | 1/2018 | Pierce et al. |
| 2018/0051322 A1 | 2/2018 | Church et al. |
| 2018/0282787 A1 | 10/2018 | Walter et al. |

FOREIGN PATENT DOCUMENTS

| | | |
|---|---|---|
| KR | 20080003402 A | 1/2008 |
| WO | 9746704 A1 | 12/1997 |
| WO | 98/56955 A1 | 12/1998 |
| WO | 01/26708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086090 A2 | 8/2007 |
| WO | 2007/121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008157696 A2 | 12/2008 |
| WO | 2009/046348 A1 | 4/2009 |
| WO | 2009046149 A1 | 4/2009 |
| WO | 2010080134 A1 | 7/2010 |
| WO | 2010/087325 A1 | 8/2010 |
| WO | 2011/143583 A1 | 11/2011 |
| WO | 2012005595 A2 | 1/2012 |
| WO | 2012/058638 A2 | 5/2012 |
| WO | 2012/110899 A2 | 8/2012 |
| WO | 2012150035 A1 | 11/2012 |
| WO | 2013/055995 A2 | 4/2013 |

(56) References Cited

FOREIGN PATENT DOCUMENTS

| WO | 2014/048083 | A1 | | 4/2014 | |
|---|---|---|---|---|---|
| WO | 2014/0163886 | A1 | | 10/2014 | |
| WO | WO-2014163886 | A1 | * | 10/2014 | ........... C12Q 1/6844 |
| WO | 2014/182528 | A2 | | 11/2014 | |
| WO | 2015/118029 | A1 | | 8/2015 | |
| WO | 2015/127183 | A2 | | 8/2015 | |
| WO | 2016081740 | A1 | | 5/2016 | |
| WO | 2017/161251 | A1 | | 9/2017 | |

OTHER PUBLICATIONS

Cao, Yi et al.,"In-situ immuno-PCR to detect antigens," The Lancet, Sep. 16, 2000, pp. 1002-1003, vol. 356.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
Extended European Search Report dated May 13, 2019 for EP Application No. 16862929.3.
Extended European Search Report dated May 21, 2019 for European Application No. 16862945.9.
International Search Report and Written Opinion based on PCT/US2018/027583 dated Jun. 29, 2018.
Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Sano, Takeshi et al. "Immuno-PCR: Very Sensitive Antigen Detection by Means of Specific Antibody-DNA Conjugates," Science, Oct. 2, 1992, pp. 120-122, vol. 258.
Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.
Soderberg, Ola et al.,"Direct observation of individual endogenous protein complexes in situ by proximity ligation," Nature Methods, Dec. 2006, pp. 995-1000, vol. 3, No. 12, Nature Publishing Group.
Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.
Extended European Search Report issued for EP Application No. 17790240.0 dated Sep. 4, 2019.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science LTD. UK, Amsterdam, NL, vol. 80, Jan. 18, 2016 (Jan. 18, 2016), pp. 67-73, XP029441324.
Dec. 18, 2014 (PCT) International Preliminary Report—App PCT/US2013/044241.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.
Benner et al. "Gene Expression analysis by massively parallel signature sequencing (MPSS) on microbead arrays". Nature Biotechnology, vol. 18, pp. 630-634 (Jun. 31, 2000).
Brenner, et al. "Gene expression analysis by massively parallel signature sequencing (MPSS) on microbead arrays". Nature Biotechnology vol. 18, pp. 630-634 (2000) doi:10.1038/76469.
Eliscovich et al. mRNA on the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.
Ginart, P et al. RNA Sequencing in Situ. Nat Biotechnol. Jun. 2014, vol. 32, No. 6; pp. 543-544; DOI: 10.1038/nbt.2921.
Grompe (1993) Nature Genetics DOI: 10.1038/ng1093-111.
Han et al. "Quantum-dot-tagged microbeads for multiplexed optical coding of biomolecules". Nature Biotechnology, vol. 19, 99. 631-635 (Jul. 31, 2001).
International Search Report and Written Opinion issued in corresponding International Application No. PCT/US2012/071398, dated Apr. 8, 2013.
Jambhekar et al. Cis-acting determinants of asymmetric, cytoplasmic RNA transport. RNA, vol. 13, pp. 625-642, 2007 (Year: 2007).
Kalivas et al. famRCA-Race: A rolling circle amplification Race for isolating a family of homologous cDNAs in one reaction . . . Preparative Biochemistry and Biotechnology, vol. 40, No. 3, pp. 177-187, Jul. 2010. (Year: 2010).
Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, First column, first paragraph; p. 1363, first column, second paragraph to second column, first paragraph; DOI: 10.1126/science.1250212.
Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).
Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year: 2009).
Office Action issued for corresponding European Patent Application No. 12780609.9, dated Sep. 23, 2015.
Polidoros et al. Rolling circle amplification—RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.
Seo, et al. Four-color DNA sequencing by synthesis on a chip using photocleavable fluorescent nucleotides. Proceeding of the National Academy of Sciences, Apr. 2005, 102 (17) 5926-5931.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.
Singer-Kruger et al. Here, there, everywhere. RNA Biology, vol. 11, No. 8, pp. 1031-1039, Aug. 2014. (Year: 2014).
Thisse et al. "High-Resolution in situ hybridization to whole-mount zebrafish embryos" 2008. Nature Protocols. vol. 3 No. 1 pp. 59-69. Doi:10.1038/nprot.2007.514.
Thisse et al. 2008 Nature protocols vol. 3 No. 1 pp. 59-69. Doi:10.1038/nprot.2007.514.
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).
Weis et al. Protein targeting to subcellular organelles via mRNA localization. Biochimica et Biophysica Acta, vol. 1833, pp. 260-273, 2013, available online Apr. 2012 (Year: 2012).
Brown et al., Review Article : In situ Hybridization with Riboprobes : An Overview for Veterinary Pathologists. Veterinary Pathology 35 : 159-167 (Year: 1998).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Choi et al.,Programmable in situ amplification for multiplexed imaging of mRNA expression. Nature Biotechnology 28 (11): 1208 (Year: 2010).

(56) References Cited

OTHER PUBLICATIONS

Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Hansen et al., Sensitive ligand-based protein quantification using immuno-PCR: A critical review of single-probe and proximity ligation assays. Biotechniques 56:217-228 (Year: 2014).
Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 the whole document.
Kuimelis et al., Cleavage properties of an oligonucleotide containing a bridged internucleotide 5-phosphorothioate RNA linkage. Nucleic Acids Research 23 (23) : 4753-4760 (Year: 1999).
Larsson, Chatarina; Grundberg, Ida; Sbderberg, Ola; Nilsson, Mats: 11 In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] the whole document.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.
Mag et al., Synthesis and selective cleavage of an oligodeoxynucleotide containing a bridged internucleotide 5'-phosphorothioate linkage. Nucleic Acids Research 19(7): 1437 (Year: 1991).
Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 abstract.
Nadji et al.,"Photochemically and Photoenzymatically Cleavable DNA," J. Am. Chem. Soc. 1992, 114, 9266-9269.
Nuovo: "Co-labeling Using In Situ PCR: A Review "Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101 the whole document.
Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year: 2012).
Srinivas et al., On the biophysics and kinetics of toehold-mediated DNA strand displacement. Nucleic Acids Research 41 (22) : 10641-10658 (Year: 2013).
Weibrecht, Irene et al., "Simultaneous Visualization of Both Signaling Cascade Activity and End-Point Gene Expression in Single Cells", Plos One, vol. 6, No. 5, May 25, 2011 (May 25, 2011).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Chen et al., "Nanoscale imaging of RNA with expansion microscopy," Nature Methods, vol. 133, No. 8, pp. 679-684 (Aug. 1, 2016).
Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Supplemental Material for Schweitzer et al. (PNAS 2000; 97(18):10113-10119) (Year: 2000).

Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
PI: Piezo Nano Positioning, 2008 (online), retrieved on Aug. 12, 2020., pp. 1-6 <https://www.pi-usa.us/fileadmin/user_upload/pi_us/files/product_datasheets/N725_Piezo_Focus_Positioner.pdf>.
Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).
Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.
Pihlak et al. "Rapid genome sequencing with short universal tiling probes" Nature Biotechnology, vol. 26, No. 6, Jun. 2008, pp. 676-684.
Lizardi "Next-generation sequencing-by-hybridization" Nature Biotechnology, vol. 26, No. 6, Jun. 2008, pp. 649-650.
Mignardi et al. "Fourth-generation sequencing in the cell and the clinic" Genome Medicine, 2014, 6:31.
Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC ID: PMC2203993.
Wang Z, Gerstein M, Snyder M. 2009. "RNA-Seq: a revolutionary tool for transcriptomics" Nat Rev Genet 10: 57-63.
Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.
Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).
Bakal C, Aach J, Church G, Perrimon N. 2007. "Quantitative morphological signatures define local signaling networks regulating cell morphology" Science 316: 1753-6.
Bang D, Church GM. 2008. "Gene synthesis by circular assembly amplification" Nat Methods 5: 37-9.
Bell J. 2004. "Predicting disease using genomics" Nature 429: 453-6.
Eid J, Fehr A, Gray J, Luang K, Lyle J, Otto G, Peluso P, Rank D, Baybayan P, Bettman B, Bibillo A, Bjornson K, Chaudhuri B, Christians F, Cicero R, Clark S, Dalai R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C,

(56) References Cited

OTHER PUBLICATIONS

Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. 2009. "Real-time DNA sequencing from single polymerae molecules." Science 323, No. 5910 (2009): 133-138.

Harris TD, Buzby PR, Babcock H, Beer E, Bowers J, Braslaysky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.

Kim JB, Porreca GJ, Song L, Greenway SC, Gorham JM, Church GM, Seidman CE, Seidman JG. 200T "Polony multiplex analysis of gene expression (PMAGE) in mouse hypertrophic cardiomyopathy" Science 316: 1481-4.

Kurimoto K, Yabuta Y, Ohinata Y, Saitou M. 2007. "Global single-cell cDNA amplification to provide a template for representative high-density oligonucleotide microarray analysis" Nat Protoc 2: 739-52.

Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.

Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.

Mitra RD, Shendure J, Olejnik J, Edyta Krzymanska O, Church GM. 2003. "Fluorescent in situ sequencing on polymerase colonies" Anal Biochem 320: 55-65.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.

Shendure J, Mitra RD, Varma C, Church GM. 2004. "Advanced sequencing technologies: methods and goals" Nat Rev Genet 5: 335-44.

Shendure JA, Porreca GJ, Church GM. 2008. "Overview of DNA sequencing strategies" Curr Protoc Mol Biol Chapter 7: Unit 7 1.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Vigneault F, Sismour AM, Church GM. 2008. "Efficient microRNA capture and bar-coding via enzymatic oligonucleotide adenylation" Nat Methods 5: 777-9.

Zhang K, Martiny AC, Reppas NB, Barry KW, Malek J, Chisholm SW, Church GM. 2006. "Sequencing genomes from single cells by polymerase cloning" Nat Biotechnol 24: 680-6.

Zhang K, Zhu J, Shendure J, Porreca GJ, Aach JD, Mitra RD, Church GM. 2006. "Long-range polony haplotyping of individual human chromosome molecules" Nat Genet 38: 382-7.

Church et al.; Center for Casual Consequences of Variation (CCV) "An NHGRI Center for Excellence in Genomic Science" http://ccv.med.harvard.edu; Wayback Machine (Jul. 3, 2011).

Church et al.; Center for Casual Consequences of Variation (CCV) "Our four Specific Aims"http://ccv.med.harvard.edu/specific_aims.htm; Wayback Machine (Aug. 13, 2011).

Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

J. H. Lee, M.D. Ph.D. presentation entitled "Population-wide Tissue-specific Functional Analysis of Human iPS Cells Using Single-Cell in Situ Sequencing" George Church Laboratory, Wyss Institute for Biology Inspired Engineering, Harvard Medical School, Boston, Jan. 10, 2010.

Terry R, Porreca G, McCarthy K, Church GM. 2008. Polonator Instrument http://www.polonator.org; Wayback Machine (Aug. 7, 2008) "Open, Affordable, Sequencing . . . ".

Terry R, Porreca G, McCarthy K, Church GM. 2008. Polonator Instrument http://www.polonator.org; Wayback Machine (Aug. 7, 2008) "The Vision".

Terry R, Porreca G, McCarthy K, Church GM. 2008. Polonator Instrument http://www.polonator.org; Wayback Machine (Aug. 7, 2008) "The Polonator Ecosystem".

Terry R, Porreca G, McCarthy K, Church GM. 2008. Polonator Instrument http://www.polonator.org; Wayback Machine (Aug. 7, 2008) "Instrument Overview".

Terry R, Porreca G, McCarthy K, Church GM. 2008. Polonator Instrument http://www.polonator.org; Wayback Machine (Aug. 7, 2008) "Protocols".

Terry R, Porreca G, McCarthy K, Church GM. 2008. Polonator Instrument http://www.polonator.org; Wayback Machine (Sep. 5, 2008) "PET (Paired End-Tag) Genomic Shotgun Library Construction Protocol".

Terry R, Porreca G, McCarthy K, Church GM. 2008. Polonator Instrument http://www.polonator.org; Wayback Machine (Sep. 5, 2008) "Emulsion PCR Protocol".

Terry R, Porreca G, McCarthy K, Church GM. 2008. Polonator Instrument http://www.polonator.org; Wayback Machine (Sep. 5, 2008) "Emulsion Breaking Protocol".

Terry R, Porreca G, McCarthy K, Church GM. 2008. Polonator Instrument http://www.polonator.org; Wayback Machine (Sep. 5, 2008) "Bead Enrichment Protocol".

Terry R, Porreca G, McCarthy K, Church GM. 2008. Polonator Instrument http://www.polonator.org; Wayback Machine (Sep. 5, 2008) "Bead Capping Protocol".

Terry R, Porreca G, McCarthy K, Church GM. 2008. Polonator Instrument http://www.polonator.org; Wayback Machine (Sep. 5, 2008) "Coverslip Aminosilanation and Arraying Protocol".

Terry R, Porreca G, McCarthy K, Church GM. 2008. Polonator Instrument http://www.polonator.org; Wayback Machine (Sep. 5, 2008) "Polony Sequence by Ligation Protocol".

Terry R, Porreca G, McCarthy K, Church GM. 2008. Polonator Instrument http://www.polonator.org; Wayback Machine (Jul. 5, 2008) "Polony Sequence Protocols".

Terry R, Porreca G, McCarthy K, Church GM. 2008. Polonator Instrument http://www.polonator.org; Wayback Machine (Sep. 5, 2008) "Help Wanted".

Terry R, Porreca G, McCarthy K, Church GM. 2008. Polonator Instrument http://www.polonator.org; Wayback Machine (Aug. 7, 2008) "Software".

Terry R, Porreca G, McCarthy K, Church GM. 2008. Polonator Instrument http://www.polonator.org; Wayback Machine (Aug. 7, 2008) "Reagent Kits".

Terry R, Porreca G, McCarthy K, Church GM. 2008. Polonator Instrument http://www.polonator.org; Wayback Machine (Sep. 5, 2008) "Run Kits".

Terry R, Porreca G, McCarthy K, Church GM. 2008. Polonator Instrument http://www.polonator.org; Wayback Machine (Sep. 5, 2008) "Paired-Leg Library Kits".

Terry R, Porreca G, McCarthy K, Church GM. 2008. Polonator Instrument http://www.polonator.org; Wayback Machine (Sep. 5, 2008) "Emulsion PCR/Bead Capping Kits".

Terry R, Porreca G, McCarthy K, Church GM. 2008. Polonator Instrument http://www.polonator.org; Wayback Machine (Sep. 5, 2008) "Enrichment Kits".

Terry R, Porreca G, McCarthy K, Church GM. 2008. Polonator Instrument http://www.polonator.org; Wayback Machine (Aug. 7, 2008) "Flow Cells".

Church GM. 2006. "Genomes for all" Sci Am 294: 46-54.

de Bakker Pi, Yelensky R, Pe'er I, Gabriel SB, Daly MJ, Altshuler D. 2005. "Efficiency and power in genetic association studies" Nat Genet 37: 1217-23.

Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39: 1202-7.

(56) References Cited

OTHER PUBLICATIONS

Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.

Risch N, Merikangas K. 1996. "The future of genetic studies of complex human diseases" Science 273: 1516-7.

Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 122:297-302.

Altshuler D, Daly MJ, Lander ES. 2008. "Genetic mapping in human disease" Science 322: 881-8.

Cookson W, Liang L, Abecasis G, Moffatt M, Lathrop M. 2009. "Mapping complex disease traits with global gene expression" Nat Rev Genet 10: 184-94.

International HapMap C. 2005. "A haplotype map of the human genome" Nature 437: 1299-320. PMC ID: PMC1880871.

Klein RJ. 2007. "Power analysis for genome-wide association studies" BMC Genet 8: 58. PMC ID: PMC2042984.

Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.

McCarroll SA. 2008. "Extending genome-wide association studies to copy-number variation" Hum Mol Genet 17: R135-42.

Morley M, Molony CM, Weber TM, Devlin JL, Ewens KG, Spielman RS, Cheung VG. 2004. "Genetic analysis of genome-wide variation in human gene expression" Nature 430: 743-7.

Sachidanandam R, Weissman D, Schmidt SC, Kakol JM, Stein LD, Marth G, Sherry S, Mullikin JC, Mortimore BJ, Nilley DL, Hunt SE, Cole CG, Coggill PC, Rice CM, Ning Z, Rogers J, Bentley DR, Kwok PY, Mardis ER, Yeh RT, Schultz B, Cook L, Davenport R, Dante M, Fulton L, Hillier L, Waterston RH, McPherson JD, Gilman B, Schaffner S, Van Etten WJ, Reich D, Higgins J, Daly MJ, Blumenstiel B, Baldwin J, Stange-Thomann N, Zody MC, Linton L, Lander ES, Altshuler D, International SNPMWG. 2001. "A map of human genome sequence variation containing 1.42 million single nucleotide polymorphisms." Nature 409, No. 6822 (2001):928-934.

Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.

Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.

Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.

Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.

Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.

Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hailer D, Daly MJ, Altshuler D. 2008. "Genetic analysis of human traits in vitro: drug response and gene expression in lymphoblastoid cell lines" PLoS Genet 4: e1000287. PMC ID: PMC2583954.

Christian AT, Pattee MS, Attix CM, Reed BE, Sorensen KJ, Tucker JD. 2001. "Detection of DNA point mutations and nRNA expression levels by rolling circle amplification in individual cells" Proc Natl Acad Sci U S A 98: 14238-43. PMC ID: PMC64666.

Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).

Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.

Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.

Kolb HC, Finn MG, B. SK. 2001. "Click Chemistry: Diverse Chemical Function from a Few Good Reactions" Angew. Chem. Int. 40: 2004-21.

Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC ID: PMC148770.

Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.

Mitra RD, Bully VL, Shendure J, Williams BR, Housman DE, Church GM. 2003. "Digital genotyping and haplotyping with polymerase colonies" Proc Natl Acad Sci U S A 100: 5926-31. PMC ID: PMC156303.

Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.

* cited by examiner

Array Synthesis Design

1. Universal sequence-based Splint Ligation

2. Second strand synthesis

Non-displacing polymerase e.g. T4/T7 polymerase

3. Type IIS Enzyme Digestion

4. Purify probe

US 11,085,072 B2

METHODS OF GENERATING LIBRARIES OF NUCLEIC ACID SEQUENCES FOR DETECTION VIA FLUORESCENT IN SITU SEQUENCING

RELATED APPLICATION DATA

This application is a continuation application, which claims priority to PCT Application No. PCT/US17/49633 designating the United States and filed Aug. 31, 2017; which claims the benefit of U.S. Provisional Application No. 62/381,980 and filed Aug. 31, 2016 each of which are hereby incorporated by reference in their entireties.

STATEMENT OF GOVERNMENT INTERESTS

This invention was made with government support under HG005550 and HG008525 awarded by the National Institutes of Health and 1144152 awarded by the National Science Foundation. The government has certain rights in the invention.

BACKGROUND OF THE INVENTION

Randomly capturing RNA sequences for in situ sequencing enables de novo measurement of both sequence variation and the spatial organization of gene expression. Yet it is recognized that for many applications, sensitive detection of a targeted subset of RNA species is incredibly valuable. For example, it is desirable to accurately detect the expressions of certain genes that are known to be clinically relevant to diagnosis, prognosis, and therapeutic guidance for human diseases. In the same way, randomly capturing DNA sequences for in situ sequencing enables de novo measurement of both sequence variation and the spatial organization of genomes and DNA molecules. Yet it is recognized that for many applications, sensitive detection of a targeted subset of DNA loci or sites of variation is incredibly valuable. For example, it is desirable to accurately detect the presence of certain genomic mutations or genotypes that are known to be clinically relevant to diagnosis, prognosis, and therapeutic guidance for human diseases. There remains a need for the development of methods that allows accurate and efficient detection of nucleic acid (i.e. DNA and RNA) via fluorescent in situ sequencing (FISSEQ).

SUMMARY OF THE INVENTION

In various instances, the present disclosure provides compositions and methods for preparing a library of sequences for florescent in situ sequencing (FISSEQ). In one aspect, the present disclosure provides a method for enhancing a hybridization reaction in a cell or cellular matrix. The method comprises: (a) providing said cell or cellular matrix and a reaction mixture, comprising (i) a target nucleic acid molecule, (ii) a probe having sequence complementarity with a target sequence of said target nucleic acid molecule, and (iii) a hybridization reaction enhancing agent comprising a polymer backbone, wherein said hybridization reaction enhancing agent enhances a rate of a hybridization reaction between said target nucleic acid molecule and said probe having sequence complementarity with said target sequence of said target molecule, and wherein said hybridization enhancing agent comprises a functional group that facilitates inactivation of said hybridization reaction enhancing agent; and (b) subjecting said reaction mixture to conditions sufficient to conduct said hybridization reaction between said target nucleic acid molecule and said probe having sequence complementarity with said target sequence of said target nucleic acid molecule, wherein during said hybridization reaction, said hybridization reaction enhancing agent enhances said rate of said hybridization reaction between said target nucleic acid molecule and said probe having sequence complementarity with said target sequence of said target molecule, as compared to another hybridization reaction conducted between said target nucleic acid molecule and said probe in the absence of said hybridization reaction enhancing agent.

In some embodiments, the present disclosure provides a method further comprising, subsequent to (b), subjecting said functional group to conditions sufficient to inactivate said hybridization reaction enhancing agent. In some embodiments, the present disclosure provides the method further comprising inactivating the hybridization reaction enhancing agent.

In some embodiments, the present disclosure provides the method further comprising initiating an enzymatic reaction, wherein the enzymatic reaction comprises reverse transcription, ligation, DNA polymerization. In some embodiments, said functional group is a hydrating group. In some embodiments, the present disclosure provides that said hydrating group is an ionic, electrolytic, or hydrophilic group.

In some embodiments, the present disclosure provides that the hybridization reaction enhancing agent comprises a cleavable linker between the polymer backbone and the hydrating group. In some embodiments, the present disclosure provides that the cleavable linker comprises alpha-hydroxy acids, beta-keto acids, disulfide linkages, or other type of chemical linkages. In some embodiments, the functional group is cleavable. In some embodiments, the method further comprises triggering cleavage of the functional group. In some embodiments, the method further comprises washing away the functional group. In some embodiments, the method further comprises initiating an enzymatic reaction. In some embodiments, the hybridization enhancing agent is further configured to enhance said enzymatic reaction. In some embodiments, the present disclosure provides that the enzymatic reaction comprises reverse transcription, ligation, DNA polymerization.

In some embodiments, the present disclosure provides said functional groups is configured to be selectively inactivated by rendering an ionic group to have a neutral charge, or by rendering the hydrating group to be weakly hydrating.

In some embodiments, the present disclosure provides method for enhancing a hybridization reaction in a cell or cellular matrix, wherein said cell or cellular matrix is integrated with a hydrogel. In some cases, said reaction mixture further comprises a buffer. In some embodiments, said buffer comprises a salt. In some embodiments, said buffer comprises blocking agents configured to reduce non-specific binding of probes to off-target sequences. In some embodiments, said buffer comprises agents configured to alter an annealing property of DNA.

In some embodiments, said polymer backbone is an ionic polymer backbone.

In some embodiments, the hybridization enhancing agent comprises a polyionic, polyelectrolyte, hydrophilic, or hydrating polymer.

In another aspect, the present disclosure provides a probe set for in situ nucleic acid sequence detection or identification of one or more target nucleic acid molecules of a cell. The probe set may comprise a plurality of probes comprising a plurality of target-specific sequences, a plurality of adaptor sequences and a plurality of barcode sequences, wherein a given probe of said plurality of probes comprises: (i) a sequence of said plurality of target-specific sequences that is complementary to a target sequence of a target nucleic acid molecule of said one or more target nucleic acid molecules of said cell; (ii) an adaptor sequence of said plurality of adaptor sequences coupled to said sequence, wherein said adaptor sequence comprises a binding site for a primer for an amplification reaction; and (iii) a barcode sequence of said plurality of barcode sequences coupled to said adaptor sequence, wherein said barcode sequence is configured to allow detection or identification of said target sequence or said at least said portion of said target nucleic acid molecule, and wherein said plurality of barcode sequences are different across said plurality of probes.

In some embodiments, the barcode sequence comprises a gene barcode corresponding to a particular gene, and wherein the gene barcode is configured to allow detection of the particular gene. In some embodiments, the barcode sequence further comprises a sequence barcode corresponding to the sequence complementary to the target region, and wherein the sequence barcode is configured to allow detection of the sequence. In some embodiments, the gene barcode is defined by a first set of sequences of the barcode sequences, and wherein the sequence barcode is defined by the remaining set of sequences of the barcode sequences. In some embodiments, said plurality of barcode sequences permit identification of different target sequences of different target nucleic acid molecules. In some embodiments, said plurality of adaptor sequences are the same across said plurality of probes. In some embodiments, said adaptor sequence is complementary to a primer for conducting said amplification reaction. In some embodiments, said amplification reaction is a rolling circle amplification (RCA) reaction. In some embodiments, a given barcode sequence of said plurality of barcode sequences permits identification of a given sequence of said target region. In some embodiments, the adaptor sequence is located between the sequence complementary to the nucleic acid molecule and the barcode. In some embodiments, the barcode sequence is located between the sequence of said plurality of target-specific sequences and the adaptor sequence. In some embodiments, said target nucleic acid molecule is ribonucleic acid (RNA), and wherein the sequence of said plurality of sequences is configured to prime reverse transcription. In some embodiments, the sequence of said plurality of target-specific sequences is located at a 3' end of each probe.

In some embodiments, the sequence of said plurality of target-specific sequences, the adaptor sequence, and the barcode sequence are arranged contiguously from the 3' end to the 5' end of said given probe. In some embodiments, a 5' end of said given probe is phosphorylated.

The present disclosure also provides a method of generating libraries of probes for detecting nucleic acid in situ with said given probe, comprising: hybridizing said given probe to a nucleic acid sequence to produce a hybridized product, and circularizing the hybridized product, and generating said libraries of probes via an amplification reaction. In some embodiments, circularizing the hybridized product comprises circularizing by a ligase when the probe is annealed to the nucleic acid sequence. In some embodiments, circularizing the hybridized product comprises circularizing by a ligase using an additional splint oligonucleotide independent of the nucleic acid sequence.

In some embodiments, circularizing the hybridized product comprises filling in a gap in the probe with aid of a reverse transcriptase, DNA polymerase, or ligase.

In some embodiments, the nucleic acid sequence is a ribonucleic acid (RNA) or complementary deoxyribonucleic acid (cDNA) sequence. In some embodiments, the nucleic acid sequence is a deoxyribonucleic acid (DNA) sequence.

In some embodiments, the plurality of probes are linear probes. In some embodiments, the plurality of probes are circular probes. In some embodiments, the plurality of probes comprise molecular inversion probes. In some embodiments, the plurality of probes comprise padlock probes. In some embodiments, said given probe of the plurality further comprises processing sites. In some embodiments, the processing sites comprise additional amplification regions. In some embodiments, the additional amplification regions comprise polymerase chain reaction (PCR) primer sequences. In some embodiments, the processing sites comprise additional cutting sites.

The present disclosure also provides a method of maturing the plurality of probes, comprising: cutting away additional amplification regions via the additional cutting sites.

In some embodiments, said given probe of the plurality comprises a sufficient length so as be circularized. In some embodiments, the sufficient length is equal to or more than 35 nucleotides.

The present disclosure also provides a method of depleting target sequences with said given probe. The method may comprise: hybridizing the probe to a nucleic acid sequence, and depleting said sequence. In some embodiments, said depleting is mediated by a RNase H digestion.

In some embodiments, said depleting is mediated by a Cas9 or other protein-nucleic acid complexes.

In another aspect, the present disclosure provides a method for in situ nucleic acid sequence detection or identification of one or more target nucleic acid molecules of a cell. The method comprises: (a) providing a reaction mixture comprising said one or more target nucleic acid molecules and a plurality of probes, wherein said plurality of probes comprises a plurality of target-specific sequences, a plurality of adaptor sequences and a plurality of barcode sequences, wherein a given probe of said plurality of probes comprises: (i) a sequence of said plurality of target-specific sequences that is complementary to a target sequence of a target nucleic acid molecule of said one or more target nucleic acid molecules; (ii) an adaptor sequence of said plurality of adaptor sequences coupled to said sequence, wherein said adaptor sequence is for conducting an amplification reaction on said given probe when said sequence is hybridized to said target sequence; and (iii) a barcode sequence of said plurality of barcode sequences coupled to said adaptor sequence, wherein said barcode sequence is configured to allow detection or identification of said target sequence or said at least said portion of said target nucleic acid molecule, and wherein said plurality of barcode sequences are difference across said plurality of probes; (b) subjecting said reaction mixture to conditions sufficient to permit said sequence to hybridize to said target sequence; and (c) using said barcode to detect or identify said target sequence or said at least said portion of said target nucleic acid molecule.

In some embodiments, the method further comprises, prior to (c), conducting said amplification reaction on said given probe when said sequence is hybridized to said target sequence.

In some embodiments, said target nucleic acid molecule is a ribonucleic acid molecule, and wherein (b) further comprises subjecting said sequence to conditions sufficient to perform reverse transcription amplification on said sequence to yield a complementary deoxyribonucleic acid molecule as an amplification product of said given probe.

In some embodiments, the barcode sequence comprises a gene barcode corresponding to a particular gene, and wherein the gene barcode is configured to allow detection of the particular gene.

In some embodiments, the barcode sequence further comprises a sequence barcode corresponding to the sequence complementary to the target region, and wherein the sequence barcode is configured to allow detection of the sequence.

In some embodiments, the gene barcode is defined by a first set of sequences of the barcode sequences, and wherein the sequence barcode is defined by the remaining set of sequences of the barcode sequences.

In another aspect, the present disclosure provides a method of generating a library of nucleic acid sequences for target nucleic acid sequence detection. The method may comprise: identifying a set of target nucleic acid sequences; designing a plurality of linear probes targeting the set of target nucleic acid sequences; hybridizing the plurality of linear probes to the target nucleic acid sequence; circularizing the plurality of linear probes; and detecting the target nucleic acid sequences by fluorescent in situ sequencing (FISSEQ).

In some embodiments, the probes are probe complexes comprising nucleic acid, DNA transposase, or Cas9. In some embodiments, the plurality of linear probes are circularized by an enzyme. In some embodiments, the enzyme comprises a ligase. In some embodiments, the enzyme further comprises a reverse transcriptase, a polymerase, or both. In some embodiments, the method further comprises amplifying the plurality of circularized probes.

In some embodiments the plurality of circularized probes are amplified by rolling circle amplification. In some embodiments, each of the plurality of probes comprises an adaptor sequence. In some embodiments, each of the plurality of probes further comprises a barcode sequence. In some embodiments, the plurality of probes are synthesized by DNA microarray. In some embodiments, the plurality of probes are hybridized to the target nucleic acid sequences in the presence of a crowding agent. In some embodiments, the sequencing is sequencing by synthesis (SBS), sequencing by ligation (SBL), or sequencing by hybridization (SBH). In some embodiments, the target nucleic acids comprise ribonucleic acids or deoxyribonucleic acids. In some embodiments, the deoxynucleic acids are double-stranded deoxynucleic acids. In some embodiments, the double-stranded deoxynucleic acids are converted into single-stranded deoxynucleic acids by thermal melting or enzymatic digestion. In some embodiments, the plurality of probes comprises nucleic acid analogs. In some embodiments, the nucleic acid analogs comprise locked-nucleic acid (LNA).

In another aspect, the present disclosure provides a method of scoring candidate nucleic acid sequences for targeted nucleic acid sequence detection. The method comprises: identifying, with aid of a processor, target nucleic acid sequences for detection; generating, with aid of the processor, a probe sequence database, wherein the probe sequence database comprises a plurality of different subsequences of the target nucleic acid sequences; scoring, with aid of the processor, the plurality of different subsequences of the probe sequence database based on a predetermined criteria for use in fluorescent in situ sequencing (FISSEQ).

In some embodiments, each of the plurality of candidate probe sequences comprise a predetermined length. In some embodiments, the predetermined length is 15 nucleotides or less. In some embodiments, said scoring is based on existence of a G quadruplex. In some embodiments, said scoring is based on guanine-cytosine content. In some embodiments, said scoring is based on a melting temperature of the plurality of different subsequences. In some embodiments, said scoring is based on an exon pileup. In some embodiments, said scoring is based on likelihood of probe heterodimerization. In some embodiments, said scoring is based on existence of common k-mers. In some embodiments, said scoring is based on a thermodynamic approach.

In some embodiments, the thermodynamic approach comprises using a Blast algorithm with a short word size to find similarities, generating a similarity matrix, and using the similarity matrix to compute thermodynamic values of the plurality of different subsequences, and eliminating subsequences based on a thermodynamic threshold for cross-hybridization. In some embodiments, said scoring is based on enzyme mismatch sensitivity profiles. In some embodiments, said scoring is based on sequence dependency of downstream fluorescent in situ sequencing (FISSEQ) steps. In some embodiments, the sequence dependency is measured using probe-level barcodes. In some embodiments, said scoring is based on five or more different criteria. In some embodiments, the method further comprises excluding, from the probe sequence database, a subset of the plurality of different subsequences of the target nucleic acid sequence. In some embodiments, the subset of the plurality of different subsequences comprises subsequences not meeting the predetermined criteria. In some embodiments, the subset of the plurality of different subsequences comprises subsequences comprising a G quadruplex. In some embodiments, the subset of the plurality of different subsequences comprises subsequences likely to undergo heterodimer formation. In some embodiments, the method further comprises selecting, from the probe sequence database, a subset of the plurality of different subsequences of the target nucleic acid sequence for synthesizing libraries of nucleic acid sequences for said targeted nucleic acid sequence detection.

In some embodiments, the method further comprises synthesizing libraries of nucleic acid sequences based on said scoring. In some embodiments, said libraries of nucleic acid sequences comprise a subset of the plurality of different subsequences selected based on said predetermined criteria. In some embodiments, the method further comprises incorporating an adaptor sequence with each of the plurality of different subsequences. In some embodiments, the adaptor sequence comprises a T2S sequencing primer. In some embodiments, the method further comprises incorporating a barcode to each of the plurality of different subsequences. In some embodiments, said assigning comprises: providing a pool of barcodes, and dentifying a set of g barcodes with Hamming distance h. In some embodiments, the pool of barcodes are derived from a pool of k-mers. In some embodiments, the pool of barcodes exclude homopolymers and GV runs >=4, or G quadruplexes. In some embodiments, said identifying the set of g barcodes with Hamming distance H is accomplished using a graph based algorithm.

In some embodiments, the method provided herein further comprises amplifying the libraries of nucleic acid sequences. In some embodiments, a fraction of the plurality of different subsequences is amplified. In some embodiments, the method further comprises purifying the libraries of nucleic acid sequences. In some embodiments, the method further comprises utilizing the libraries of nucleic acid sequences. In some embodiments, said utilizing the plurality of different subsequences comprises utilizing the plurality of different subsequences in fluorescent in situ sequencing (FISSEQ).

In another aspect, the present disclosure provides a method of generating libraries of nucleic acid sequences for targeted nucleic acid sequence detection, the method comprising: identifying a set of target nucleic acid sequences for detection; generating reference sequence databases comprising sequence portions from the set of target nucleic acid sequences; selecting candidate sequence portions from the reference sequence databases; designing, computationally, the libraries of nucleic acid sequences, wherein said designing comprises scoring said candidate sequence portions according to a predetermined criteria; synthesizing the libraries of nucleic acid sequences; amplifying the libraries of nucleic acid sequences; purifying the libraries of nucleic acid sequences; and validating the libraries of nucleic acid sequences for targeted nucleic acid sequence detection, wherein the targeted nucleic acid sequence detection is via fluorescent in situ sequencing (FISSEQ). In some embodiments, the libraries of nucleic acid sequences comprise a sequence portion that is complementary to the candidate sequence portion of the target nucleic acid sequences.

In some embodiments, the libraries of nucleic acid sequences further comprise adaptor sequence. In some embodiments, the libraries of nucleic acid sequences further comprise a barcode sequence. In some embodiments, the libraries of nucleic acid sequences are complexed with one or more proteins. In some embodiments, the libraries of nucleic acid sequences are synthesized on a DNA microarray. In some embodiments, the libraries of nucleic acid sequences comprise guide RNAs that are complexed CRISPR enzymes for FISSEQ detection of the guide RNAs, and wherein each of the guide RNAs comprises an adaptor sequence. In some embodiments, the method comprises validating the nucleic acid sequences, wherein validating the nucleic acid sequences is by sequencing by synthesis (SBS), sequencing by ligation (SBL), or sequencing by hybridization (SBH). In some embodiments, targeted nucleic acid sequence detection is by sequencing by synthesis (SBS), sequencing by ligation (SBL), or sequencing by hybridization (SBH).

In some embodiments, the libraries of nucleic acid sequences are hybridized to the set of target nucleic acid sequences in situ for detection. In some embodiments, a crowding agent is included for enzyme-compatible enhancement of hybridization between the libraries of nucleic acid sequences and the set of target nucleic acid sequences. In some embodiments, the method further comprises circularizing the library of nucleic acid sequences hybridized to the target nucleic acid sequences. In some embodiments, the library of nucleic acid sequences is circularized by an enzyme. In some embodiments, the enzyme comprises a ligase. In some embodiments, the enzyme further comprises a reverse transcriptase, a polymerase, or both.

In some embodiments, the library of nucleic acid sequences is circularized when hybridized to a splint oligonucleotide. In some embodiments, the circularized library of nucleic acid sequences are amplified by rolling circle amplification. In some embodiments, the target nucleic acids comprise ribonucleic acids or deoxyribonucleic acids. In some embodiments, the deoxynucleic acids are double-stranded deoxynucleic acids. In some embodiments, the double-stranded deoxynucleic acids are converted into single-stranded deoxynucleic acids by thermal melting or enzymatic digestion. In some embodiments, the library of nucleic acid sequences comprises nucleic acid analogs. In some embodiments, the nucleic acid analogs comprise locked-nucleic acid (LNA).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Targeted FISSEQ

Figure 1A:
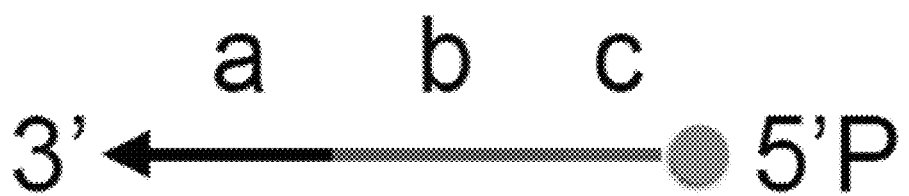
FIG. 1A illustrates a mature primer comprising: (a) sequence complementary to the RNA molecule at the 3' end, which anneals to the RNA molecule in situ and primes RT; (b) a common adaptor sequence, from which RCA and sequencing reactions are primed; (c) a gene-level barcode at the 5' end; and 5' phosphorylation, in accordance with embodiments.

Fluorescent in situ sequencing (FISSEQ) can refer to a method to detect or sequence 3-dimensionally arranged targets in situ within a matrix, wherein the detection signal is a fluorescent signal. Sequencing methods that can be employed by FISSEQ can be sequencing-by-synthesis, sequencing by ligation, or sequencing by hybridization. The targets detected or sequenced in FISSEQ can be a biomolecule of interest or a probe bound to the biomolecule of interest.

Targeted FISSEQ may have the potential for greater per-molecule sensitivity, as cellular volume that would otherwise be occupied by RCA amplicons containing cDNA or DNA sequence irrelevant to a biological phenomenon can be reallocated to the subset of RNA or DNA species of interest. Moreover, for RNA capture, random hexamer priming of reverse transcription may not be particularly efficient. See e.g., Ståhlberg, Anders, et al. "Properties of the reverse transcription reaction in mRNA quantification." *Clinical chemistry* 50.3 (2004): 509-515. In some instances, targeted FISSEQ may have a sensitivity equal to or greater than about 5 times, 10 times, 20 times, 40 times, 80 times, 120 times, 160 times, 200 times, 400 times, 1000 times, 5000 times, or more of that of that of random FISSEQ. For example, assuming that a RCA amplicon occupies 0.04 um^3 intracellular volume, approximately corresponding to the volume of a diffraction-limited voxel under standard microscopy conditions, human cells range in average approximate a volume from 100 um^3 (erithrocytes) to 4,000,000 um^3 (oocytes), corresponding to a maximum of 2,500 to 100,000,000 diffraction-limited voxels per human cell, depending on type. At the lower end, many human cells, such as erythrocytes, neutrophils, beta cells, enterocytes, fibroblasts, and so on, can contain fewer than approximately 100,000 diffraction-limited voxels. However, a typical mammalian cell may contain as many as 500,000 mRNA molecules, corresponding to tens of thousands of genetic species. GAPDH, a house-keeping gene, is commonly assumed to be expressed at a copy number of 500 molecules per cell. Given an erythrocyte with volume of 100 um^3 and containing 500,000 mRNA molecules, a perfect space-filling FISSEQ method could detect as many as 0.5% of mRNA molecules, or approximately on average 2.5 of the 500 GAPDH molecules, if sampled randomly. However, a targeted GAPDH FISSEQ assay with optimized efficiency of 80% per-molecule capture, comparable to estimates of single molecule FISH sensitivity, would detect on average approximately 400 of the 500 GAPDH molecules, representing a 160-fold improvement in sensitivity. For lower-expressed genes, such as transcription factors, which may be expressed at only a few copies of RNA per cell (say, 5 molecules per cell), untargeted FISSEQ may detect on average zero molecules per cell, whereas an 80% per-molecule efficient targeted FISSEQ assay would detect 4 of 5 transcription factor RNA molecules, representing a nearly infinite improvement in sensitivity. Moreover, for RNA capture, random hexamer priming of reverse transcription may not be efficient. Other sequence capture methodologies and probe designs may have better capture efficiencies. For DNA capture, targeted capture may also benefit from enhanced per-molecule sensitivity.

Targeted FISSEQ can also be a substantially faster assay than whole transcriptome RNA FISSEQ or whole genome DNA FISSEQ. In some instances, targeted FISSEQ may be about 2 times, 3 times, 4 times, 6 times, 8 times, 10 times, 12 times, 14 times, 16 times, 18 times, or 20 times faster than whole transcriptome RNA FISSEQ or whole genome DNA FISSEQ. As one example, whole-transcriptome FISSEQ may require a sequencing read long enough for high-precision short read alignment. In other words, the sequencing read may need to be long enough to computationally determine the originating molecular species, such as by alignment of the sequencing read to a genomic or transcriptomic reference sequence database. In such whole-omic applications, RNA-seq reads may need to be approximately 20-30 bases long, while genomic reads may need to be longer, such as 50-100 bases long, in order to recover substantially accurate alignments. For targeted FISSEQ of barcode molecular labels, where the barcode labels may understood to be nucleic acid sequences with $4^N$ complexity given a sequencing read of N bases, a much shorter sequencing read may be required for molecular identification. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. Therefore, a targeted FISSEQ assay designed to detect each gene in the human transcriptome may be nearly 4× faster (8 bases vs 30 bases), and in the human genome up to more than 12× faster (8 bases vs 100 bases). When targeting specific RNA species for reverse transcription, the space of potential cDNA sequences can be a significant subset of the entire transcriptome, and therefore fewer bases of sequencing are required to identify the target molecule. When targeting specific DNA loci or nucleotides for sequencing or re-sequencing, the space of captured sequences can be a significant subset of the entire genomic sequence or cellular DNA sequence. Targeted FISSEQ strategies where molecular "barcode" sequences contained in the probes are detected, rather than endogenous sequences, can be an efficient read-out in terms of information per cycle of sequencing. Because the barcode sequences are pre-determined, they can also be designed to feature error detection and correction mechanisms.

The targeted FISSEQ can be applied to any sample from which spatial information is of interest. For example, the sample can be a biological sample, including a cell, a tissue, and a cellular matrix. Depending on the application, the biological sample can also be whole blood, serum, plasma, mucosa, saliva, cheek swab, urine, stool, cells, tissue, bodily fluid or a combination thereof.

The present disclosure provides for various targeted nucleic acid FISSEQ library construction methods. Therefore, even though the disclosure will not explicitly enumerate all possible implementations, it should be understood that the general descriptions of these approaches can be extended or combined in a variety of ways. These strategies may vary in the number and type of enzymatic reactions required to construct the in situ sequencing library, from the most elaborate (e.g. a targeted RNA FISSEQ method closely mirroring the random capture protocol, but using a pool of specific RT primers), to the simplest methods requiring no enzymatic reactions, only nucleic acid hybridization.

The term "nucleic acid" as used herein may refer to a molecule comprising one or more nucleic acid subunits, or nucleotides, and can be used interchangeably with "polynucleotide" or "oligonucleotide". A nucleic acid may include one or more nucleotides selected from adenosine (A), cytosine (C), guanine (G), thymine (T) and uracil (U), or variants thereof. A nucleotide may include a nucleoside and at least 1, 2, 3, 4, 5, 6, 7, 8, 9, 10, or more phosphate (PO3) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid can be single-stranded, double-stranded, triple-stranded, helical, hairpin, etc. In some cases, a nucleic acid molecule is circular. A nucleic acid can have various lengths. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. A nucleic acid molecule can be isolated from a cell or a tissue. As embodied herein, the nucleic acid sequences may comprise isolated and purified DNA/RNA molecules, synthetic DNA/RNA molecules, synthetic DNA/RNA analogs.

Nucleic acid analogs can include, but are not limited to, 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (LNAs). Further exemplary inhibitory nucleic acids include modified oligonucleotides (2'-O-methylated or 2'-O-methoxyethyl), locked nucleic acids (LNA), morpholino oligonucleotides, peptide nucleic acids (PNAs), PNA-peptide conjugates, and LNA/2'-O-methylated oligonucleotide mixmers. For exemplary modifications see, e.g., Valóczi et al., Nucleic Acids Res. 32(22):e175 (2004) Fabiani and Gait, RNA 14:336-46 (2008); Lanford et al., Science 327(5962: 198-201 (2010); Elmen et al., Nature 452:896-9 (2008); Gebert et al., Nucleic Acids Res. 42(1):609-21 (2013); Kloosterman et al., PLoS Biol 5(8):e203 (2007); and Elmen et al., Nucleic Acids Res. 36:1153-1162 (2008).

Additional examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid(v), 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July;8(7): 612-4, which is herein incorporated by reference for all purposes.

Enzymatic reactions can be challenging to optimize in situ, and are a likely source of reduced capture efficiency per target molecule. However, enzymatic reactions can also increase the amount of information captured in the FISSEQ library. For example, reverse transcription is necessary for de novo detection of RNA sequences, including variation due to RNA editing, alternative splicing, or gene fusions. Without using an enzyme to capture RNA-templated sequence, or to catalyze a base mismatch-sensitive reaction, nucleic acid hybridization alone can be dependent upon to confer specificity on the probe-target interaction. In some embodiments, the mismatch sensitivity of Cas9 or another nucleic acid-guided, nucleic acid-binding protein may be used to enhance the capture specificity of a DNA sequence.

In some embodiments, targeted FISSEQ methods provided herein comprises a pool, or library, of short oligonucleotide probes to specifically capture certain nucleic acid molecules. The term "probe" used herein can refer to an oligonucleotide that can bind to a biomolecule target in a sample. The probe can directly or indirectly bind to the target. The probe can be in various lengths. To reduce the cost of synthesizing the probe pools, in some embodiments, microarray DNA synthesis platforms can be used to generate massively complex short (approximately 200 nucleotide) oligonucleotide libraries. See e.g., Kosuri, Sriram, and George M. Church. "Large-scale de novo DNA synthesis: technologies and applications." *Nature methods* 11.5 (2014): 499-507. Exemplary platforms may include platforms provided by Agilent, CustomArray, and Twist Bioscience. Microarray synthesis may refer to the synthesis of DNA or nucleic acid analog oligonucleotides attached to a solid substrate. Commercial supplier Twist Bioscience, for example, features microarrays containing 9,600 wells with 121 discrete oligonucleotide species synthesized per well, for a total of 1.16 million oligonucleotides per array. Commercial supplier Agilent's OLS libraries contain just over 244,000 oligonucleotide species, while the DNA microarray of commercial supplier Custom Array synthesizes just over 94,000. These libraries of oligonucleotides are typically liberated from the solid support substrate into a solution of DNA species representing a renewable source of single-stranded DNA probes, generated using techniques to highly amplify and process the library. See e.g., Beliveau, Brian J., Nicholas Apostolopoulos, and Chao-ting Wu. "Visualizing genomes with Oligopaint FISH probes." *Current Protocols in Molecular Biology* (2014): 14-23; Chen, Kok Hao, et al. "Spatially resolved, highly multiplexed RNA profiling in single cells." *Science* 348.6233 (2015): aaa6090). Alternatively, the oligonucleotides may be amplified directly from the solid support, in whole or in specific subpools. See e.g., Kosuri, Sriram, et al. "Scalable gene synthesis by selective amplification of DNA pools from high-fidelity microchips." *Nature biotechnology* 28.12 (2010): 1295-1299.

To enable the microarray synthesis strategy, additional sequences for amplification and subsequent processing and maturation of the probes can be added to the probes. Software to facilitate computational design of the probe sequences, as well as validation by high-throughput sequencing of the final products are discussed herein. The detailed descriptions of these strategies are presented in the section on DNA Array Synthesis of Probe Pools.

Accordingly, the present disclosure provides that targeted FISSEQ can be used to detect, identify, quantify, and/or determine the nucleotide sequences of a subset of the whole transcriptome or whole genome of a biological sample.

In various embodiments, the present disclosure provides methods of targeting nucleic acid detection via FISSEQ to a subset of the whole transcriptome or whole genome. In some embodiments, the present disclosure provides methods to select a subset of targets from the whole transcriptome or whole genome. In some embodiments, the present disclosure provides methods to design probes for the target detection. In some embodiments, the present disclosure provides methods to synthesize probes for the target detection. The disclosure provides that certain novel methods of targeting nucleic acid detection via FISSEQ presented here utilize DNA microarray synthesis of oligonucleotide "libraries". In some embodiments, the present disclosure provides different probe design strategies, resulting in probes having different architectures. In some embodiments, the present disclosure provides methods to mature probes, resulting in probes suitable for FISSEQ target detection. The term "maturation" and "maturing" used herein may refer to a process to make a probe or a probe library suitable to be used in the FISSEQ assay. For example, in some cases, a probe library synthesized from the DNA microarray may need to be further amplified before using in FISSEQ. In these cases, an amplification primer may be incorporated in each of the probe in the original probe library for amplification, but needs to be cleaved after amplification to mature the probe library.

Targeted FISSEQ can exhibit several benefits, such as enhanced sensitivity and/or shorter assay time in the detection, identification, quantification, and/or determining the nucleotide sequence of the target species, relative to "random" or "whole-omic" detection via FISSEQ.

Targeted RNA Capture

Capture by Reverse Transcription

Specific reverse transcription (RT) primers rather than random primers can be used for RNA FISSEQ and can exhibit several advantages as discussed above. However, challenges remain for targeting RNA species using specific RT primers rather than random primers. For example, while in prior studies, targeting of the mCherry mRNA, was possible, this transcript was expressed at a much higher level than most endogenous genes. See e.g., Lee, Je Hyuk, et al. "Highly multiplexed subcellular RNA sequencing in situ." *Science* 343.6177 (2014): 1360-1363. Among the RT primers that were targeted to mCherry mRNA, it was observed that the efficiency of RNA capture fall dramatically as the target site moved away from the 5' end of the transcript. Since this experiment also used a targeted rolling circle amplification (RCA) primer complementary to cDNA sequence just after the annotated transcription start site, the RT primer position-dependent variation in efficiency could be due to either inefficient circularization of the longer cDNA molecules or reverse transcription terminating prematurely, before reaching the RCA priming sequence. It remains as a challenge to rationally design targeted RT primers against other genes to generate appreciable numbers of RCA amplicons. Given that the logic of RNA accessibility in situ was not fully understood—for example, which regions of RNA transcripts are generally bound by paused or dense polysome complex—nor the sequence dependency of reverse transcriptase, one approach to targeted RT for FISSEQ of the present disclosure is to massively tile target species with RT primers. In some instances, a target RNA or DNA species may be massively tiled by targeted capture probes by designing a plurality of probes complementary in part, or substantially complimentary in part, to the entirety of the nucleic acid species in aggregate. In such instances, a target RNA species k bases long may have k targeting primers. For example, a pool of targeted reverse transcription primers with 20-nucleotides of sequence complementarity, or substantial sequence complementarity, to the target species, may contain a primer complementary or substantially complementary to bases 1-20, another complementary or substantially complementary to bases 2-21, and so on, with the last primer complementary or substantially complementary to the bases (k-20) to k, where the target species is k bases long. In other instances, the pool of targeted primers may comprise 1-10, 10-100, 100-1000, or 1 to k primers.

Figure 1B:
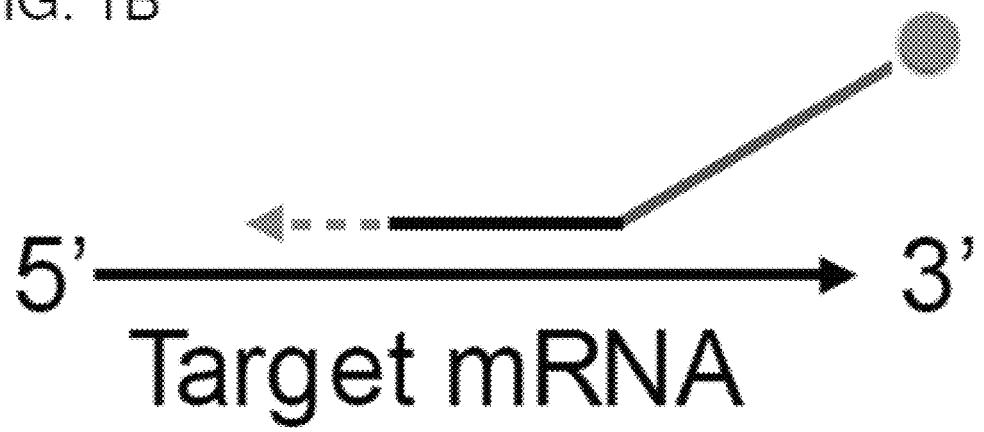
FIG. 1B illustrates that the complementary region of the primer anneals to the target RNA species and primes an RT reaction, incorporating RNA-templated bases into the cDNA, in accordance with embodiments.
Figure 1C:
FIG. 1C illustrates that in the linear RCA amplicon, each of the n tandem repeats contains the barcode as well as adjacent RNA-templated sequence, enabling quantification of capture specificity, in accordance with embodiments.

To facilitate fast detection, a barcoded FISSEQ strategy can be used, which reduces the number of sequencing cycles necessary to detect the molecular identity of each RCA amplicon (DNA nanoball). In some embodiments, a mature targeted RT primer can include the following features: a sequence complementary to the RNA molecule at the 3' end, which anneals to the RNA molecule in situ and primes RT; a common adaptor sequence, from which RCA and sequencing reactions are primed; a gene-level barcode at the 5' end; and 5' phosphorylation (FIGS. 1A-1C). The term "gene-level barcode" used herein can refer to a barcode sequence specific to a particular gene. In some embodiments, a unique barcode may be used to for one or more genes. As used herein, the terms gene-level barcode and gene barcode may be used interchangeably.

The gene-level barcode can be in various lengths, for example, 1-3 nucleotides in length, 3-5 nucleotides in length, 5-8 nucleotides in length, 8-10 nucleotides in length, or 10-15 nucleotides in length. In some embodiments, the gene-level barcode can be 2, 3, 4, 5, 6, 7, 8, 9, 10, 11, 12, 13, 14, 15, 16, 17, 18, 19, or 20 nucleotides in length. In some embodiments, the gene-level barcode may be more than 20 nucleotides in length. For example, the gene-level barcode can be designed to be 5 nucleotides in length, in theory allowing for up to $4^5$ (1024) genes to be targeted simultaneously. In practice, the number of usable barcodes, given a barcode length of k bases, may be less than $4^k$ due to the limitations of probe design and synthesis, which are discussed in the section on array synthesis. By designing RT primers containing a gene-level barcode on the 5' end, sequencing by ligation may be in the more efficient 5' direction. Moreover, by sequencing additional bases beyond the barcode we may acquire endogenous cDNA sequence, as the bases 5' of the barcode on the sequencing template correspond to the last RNA-templated bases of the linear cDNA (see FIG. 1C).

Targeted FISSEQ libraries for a number of sets of genes can be synthesized, including the clinically relevant Oncotype Dx, in order to demonstrate the use of FISSEQ for making diagnostic and prognostic determinations for human cancer. See e.g., Cronin, Maureen, et al. "Analytical validation of the Oncotype DX genomic diagnostic test for recurrence prognosis and therapeutic response prediction in node-negative, estrogen receptor-positive breast cancer." *Clinical chemistry* 53.6 (2007): 1084-1091. Targeted RNA FISSEQ datasets can be analyzed for other applications, including cellular developmental programming and detection of individual neuronal connections for connectomic reconstruction.

RT efficiency can be dependent on various factors including the primer sequence, RNA secondary structure, and/or polysome and protein occupancy on the RNA. In some instances, a unique probe barcode sequence may be coupled or incorporated into RT primers. By incorporating a unique probe barcode sequence into each RT primer, the barcode can be utilized to directly measure both the capture efficiency and specificity of each primer. Because each molecule of template is likely to acquire a unique barcode from the random barcode pool, the number of original transcript that are transcribed can be counted by counting the number of unique barcode. While this strategy can be useful for empirically screening primers and investigating the logic of efficient in situ RNA sequence capture by RT, barcoding each probe can reduce the overall number of genes that can be simultaneously detected given a particular barcode length. This during primer design can be mitigated by using the first x bases for the gene-level barcode (theoretical maximum $4^x$ genes), then the next y bases for the probe barcode (theoretical maximum $4^y$ probes per gene), with the probe barcodes being degenerate at the gene level. As used herein, a probe barcode may also be referred to as a sequence-level barcode, or a sequence barcode. In some instances, the gene-level barcode and the probe may be contiguous. Optionally, the gene barcode and the probe barcode may or may not share common nucleotide bases.

In one example, we designed initial RT primer optimization libraries specifically targeting the beta actin mRNA and the ribosomal RNA 18S. For probes targeting 18S rRNA, priming in helix 19 exhibited the greatest efficiency, although we also had high efficiency targeting helix 22. This result agrees in part with previous studies which related to measurement of 18S rRNA accessibility to FISH. See e.g., *Applied and Environmental Microbiology* 69.3 (2003): 1748-1758. The probe barcode can be in various lengths, for example, 1-3 nucleotides in length, 3-5 nucleotides in length, 5-8 nucleotides in length, 8-10 nucleotides in length, or 10-15 nucleotides in length. In some embodiments, the probe barcode can be 2, 3, 4, 5, 6, 7, 8, 9, 10, 11, 12, 13, 14, 15, 16, 17, 18, 19, or 20 nucleotides in length. In some embodiments, the probe barcode may be more than 20 nucleotides in length.

Capture by Circularization

In some instances, the probe capturing a target can be circularized. In some embodiments, the probe capturing a target can be circularized after reverse transcription. In some embodiments, the probe capturing a target can comprise sequence regions at both 5' and 3' ends of the probe that are complementary to a target sequence so that it circularizes after hybridizing to the target. In some embodiments, the probe capturing a target can be circularized with ligase. In some embodiments, the probe capturing a target can comprise a gap region after hybridizing to a target. In some embodiments, the probe capturing a target can be circularized by using a nucleic acid polymerase to fill in the gap region and followed by ligase.

In order to amplify a molecular probe using RCA, a circular DNA template may be required. A circular probe may be localized to a target RNA using various methods. For example, RT followed by ssDNA circularization is one method of localizing a circular probe molecule to a target RNA. Two other "capture by circularization" techniques, using padlock probes and molecular inversion probes (MIPs), may avoid circularization of ssDNA in favor of splint ligation (FIG. 3). Both types of probes (e.g., padlock probes and/or MIPs) may contain sequence regions at both 5' and 3' ends of the probe that are complementary to a target sequence. MIPs may contain a gap between the 5' and 3' ends that is filled by a polymerase or ligase, incorporating templated bases or complementary oligonucleotides into the probe. The MIP may be circularized by a ligase when the 3' end meets the 5' end. See e.g., Hardenbol, Paul, et al. "Multiplexed genotyping with sequence-tagged molecular inversion probes." *Nature biotechnology* 21.6 (2003): 673-678. For padlock probes, the 5' and 3' ends may be adjacent to one another when annealed, and may be ligated directly. See e.g., Nilsson, Mats, et al. "Padlock probes: circularizing oligonucleotides for localized DNA detection." *Science* 265.5181 (1994): 2085-2088. In both cases, the DNA ligase may enforce specificity during circularization of the probe by virtue of its mismatch sensitivity. Capture by circularization can be achieved by either targeting the RNA directly, or by targeting cDNA.

RNA Splint Ligation

In some embodiments, the probe can be ligated through splint ligation by a ligase. In some embodiments, the ligase may be T4 DNA ligase or SplintR.

Both padlock probes and MIPs can be hybridized directly to RNA. Targeting RNA molecules directly for capture by circularization may have the advantage of not requiring cDNA synthesis. T4 DNA ligase, in addition to its conventional activity on DNA substrates, can catalyze the ligation of nicked DNA within a hybrid DNA:RNA duplex. See e.g., Nilsson, Mats, et al. "Enhanced detection and distinction of RNA by enzymatic probe ligation." *Nature biotechnology* 18.7 (2000): 791-793; Christian, Allen T., et al. "Detection of DNA point mutations and mRNA expression levels by rolling circle amplification in individual cells." *Proceedings of the National Academy of Sciences* 98.25 (2001): 14238-14243; Nilsson, Mats, et al. "RNA-templated DNA ligation for transcript analysis." *Nucleic acids research* 29.2 (2001): 578-581. In some instances, ligases, such as SplintR (NEB) may catalyze this ligation with even greater efficiency. See e.g., Lohman, Gregory J S, et al. "Efficient DNA ligation in DNA-RNA hybrid helices by Chlorella virus DNA ligase." *Nucleic acids research* 42.3 (2014): 1831-1844. SplintR may in some instances exhibit good mismatch detection properties. Optionally, properties, such as good mismatch detection properties of DNA ligase may be used to capture a MIP directly on an RNA molecule, ligating in short oligonucleotides to fill the gap. In some instances, a MIP may be used against an RNA target, using a reverse transcriptase or DNA polymerase with reverse transcriptase activity to incorporate RNA-templated bases into the circular probe. See e.g., Moser, Michael J., et al. "Thermostable DNA polymerase from a viral metagenome is a potent RT-PCR enzyme." *PLoS One* 7.6 (2012): e38371.

A polymerase may be used to generate RCA products from a hybrid RNA:circular-DNA complex described above. For example, a Phi29 DNA polymerase can synthesize an RCA product from the hybrid RNA:circular-DNA complex by digestion of the RNA molecule via 3' exonucleotide activity until the 3' end primes the circular template. Previous demonstrations of this approach, however, have been restricted to sequences near the 3'-end of the RNA. See e.g., Stougaard, Magnus, et al. "In situ detection of non-polyadenylated RNA molecules using Turtle Probes and target primed rolling circle PRINS." BMC biotechnology 7.1 (2007): 1; Lagunavicius, Arunas, et al. "Duality of polynucleotide substrates for Phi29 DNA polymerase: 3'→5' RNase activity of the enzyme." RNA 14.3 (2008): 503-513. In some instances, the 3' end of the RNA may be required to be in close proximity to the circular template, and RNA secondary structure formation may inhibit Phi29 3' exonuclease activity, preventing it from degrading longer stretches of RNA and priming RCA. This limitation could be avoided, for example, by introducing a separate RCA priming region on the probe as disclosed in the present disclosure.

cDNA Splint Ligation

In some embodiments, the RNA target can be first reverse transcribed into a cDNA molecule, either specifically or non-specifically, and then the cDNA molecule can be captured by a probe. In some instances, the probe may be a MIP or padlock probe described herein. Ligation of dsDNA using DNA ligase may occur with greater efficiency and/or with higher mismatch sensitiv than ligation of a hybrid duplex. See e.g., Lagunavicius, Arunas, et al. "Duality of polynucleotide substrates for Phi29 DNA polymerase: 3'→5' RNase activity of the enzyme." RNA 14.3 (2008): 503-513; Bullard, Desmond R., and Richard P. Bowater. "Direct comparison of nick-joining activity of the nucleic acid ligases from bacteriophage T4." Biochemical Journal 398.1 (2006): 135-144. See also Sriskanda, Verl, and Stewart Shuman. "Specificity and fidelity of strand joining by Chlorella virus DNA ligase." Nucleic acids research 26.15 (1998): 3536-3541. In some instances, ligation of dsDNA using DNA ligase may occur with $k_{cat}/K_m$ equal to or greater than 10, $10^2$, $10^3$, $10^4$, $10^5$, $10^6$, $10^7$ or any value therebetween. Both MIP and/or padlock probe capture against cDNA can be used for multiplex detection of RNA molecules in situ. See e.g., Ke, Rongqin, et al. "In situ sequencing for RNA analysis in preserved tissue and cells." Nature methods 10.9 (2013): 857-860; Mignardi, Marco, et al. "Oligonucleotide gap-fill ligation for mutation detection and sequencing in situ." Nucleic acids research 43.22 (2015): e151-e151. Due to the use of reverse transcription, however, these strategies may have limited capture efficiency (per-molecule capture efficiency ≤30%). See e.g., Larsson, Chatarina, et al. "In situ detection and genotyping of individual mRNA molecules." Nature methods 7.5 (2010): 395-397. In some embodiments, the RT primer region of the probe can comprise nucleotide analogs such as LNA bases. RT primers containing LNA bases (Exiqon) may be used to increase hybridization efficiency in situ and also increase amplicon density for downstream padlock probe capture. See e.g., Larsson, Chatarina, et al. "In situ detection and genotyping of individual mRNA molecules." Nature methods 7.5 (2010): 395-397; Ke, Rongqin, et al. "In situ sequencing for RNA analysis in preserved tissue and cells." Nature methods 10.9 (2013): 857-860. LNA-containing primers can also be designed for resistance to RNase H such that the localization of the cDNA can be maintained by annealing to the cross-linked RNA molecule. See e.g., Kurreck, Jens, et al. "Design of antisense oligonucleotides stabilized by locked nucleic acids." Nucleic acids research 30.9 (2002): 1911-1918; Ke, Rongqin, et al. "In situ sequencing for RNA analysis in preserved tissue and cells." Nature methods 10.9 (2013): 857-860. LNA modifications can be incorporated into the synthesis of a nucleic acid probe or introduced during PCR for amplification of LNA-RT primers from array-synthesized oligonucleotide libraries. See e.g., Veedu, Rakesh N., Birte Vester, and Jesper Wengel. "Enzymatic incorporation of LNA nucleotides into DNA strands." ChemBioChem 8.5 (2007): 490-492.

Without Target-Molecule Splint Ligation

In some embodiments, it may be possible to circularize a linear capture probe in situ, targeted either to RNA or cDNA, but using another oligonucleotide as the splint for ligation, rather than the target nucleic acid. This strategy may rely on hybridization alone to confer specificity of the probe-target interaction, but may avoid some problems that arise when using the target molecule as the splint. For example, if both the probe and the splint oligonucleotide are composed of DNA, the splint ligation reaction is likely to be efficient.

In some embodiments, hybridizing circular probes directly to the RNA molecule can be used, avoiding the in situ circularization step entirely. In some instances, potential problems can arise from this strategy due to the different properties of circular ssDNA compared to linear ssDNA. Linear ssDNA may be a flexible polymer, with a persistence length in the order of a few nanometers. See e.g., Smith, Steven B., Yujia Cui, and Carlos Bustamente. "Overstretching B-DNA: the elastic response of individual double-stranded and single-stranded DNA molecules." Science 271.5250 (1996): 795; Tinland, Bernard, et al. "Persistence length of single-stranded DNA." Macromolecules 30.19 (1997): 5763-5765). Circular ssDNA may have a significantly longer persistence length. See e.g., Rechendorff, Kristian, et al. "Persistence length and scaling properties of single-stranded DNA adsorbed on modified graphite." The Journal of chemical physics 131.LPMV-ARTICLE-2009-002 (2009): 095103. This may reduce the diffusion rate of the probe into the FISSEQ hydrogel as a circular ssDNA typically migrates more slowly than the linear molecule during acrylamide gel electrophoresis. In some cases, circularization of one DNA molecule onto another linear DNA molecule may topologically link the molecules. It may be possible to hybridize a circular DNA molecule with a linear DNA molecule without introducing a strand break, i.e., without topologically linking them, by the region of the circular DNA not participating in base-pairing winding back around the target strand the same number of times as the number of helical turns of the duplex. In some embodiments, hybridization of a circularized probe to a target can exhibit greater specificity than a linear probe, possibly due to the bending force or tension created by the locked circular conformation. See e.g., Tang, Yaqin, et al. "Tension promoted circular probe for highly selective microRNA detection and imaging." Biosensors and Bioelectronics 85 (2016): 151-156. These molecules, however, are not constrained by topology due to the short length of the miRNA.

In some embodiments, a target can be bound by a number of probes. Because RCA massively amplifies the probe, any probe bound off-target or retained non-specifically within the sample can generate a false positive capture event. In some instances, it may be difficult to determine, using only a single probe, whether an amplified probe is localized to a target molecule. However, strategies for error detection and error correction using multiple capture probes per molecule can be devised. For example, the complete barcode sequence might be distributed among a number of probes. The likelihood of spatially co-localized off-target binding or non-specific retention of multiple probes corresponding to the same target molecule is small.

Using Proteins which Exhibit Binding or Other Reactivity to Nucleic Acids

In some embodiment, the probe capturing a target can be a probe complex comprising a protein component and a nuclei acid component. The protein component can facilitate binding of the probe onto the target.

In some embodiments, nucleic-acid binding proteins, such as Cas9, can be used to design targeted RNA FISSEQ methods. In some other embodiments, proteins that catalyze nucleic acid reactions other than binding, such as cleavage or ligation, may be directed to the detection of certain RNA or cDNA species. Completely programmable RNA-binding proteins can be generated using concatamers of engineered Pumilio homology domains which may be linked to a nucleic acid label (as by mRNA display, ribosome display, or conjugation of a nucleic acid tag). See e.g., Adamala, Katarzyna P., Daniel A. Martin-Alarcon, and Edward S. Boyden. "Programmable RNA-binding protein composed of repeats of a single modular unit." *Proceedings of the National Academy of Sciences* 113.19 (2016): E2579-E2588.

In some embodiments, nucleic acid-guided nucleic acid binding proteins can be used. Exemplary nucleic acid-guided nucleic acid binding proteins may include Argonaute, Cas9, Cpf1, and/or C2c2. See e.g., Bouasker, Samir, and Martin J. Simard. "Structural biology: tracing Argonaute binding." *Nature* 461.7265 (2009): 743-744); Mali, Prashant, et al. "RNA-guided human genome engineering via Cas9." *Science* 339.6121 (2013): 823-826; Cpf1 (Zetsche, Bernd, et al. "Cpf1 is a single RNA-guided endonuclease of a class 2 CRISPR-Cas system." *Cell* 163.3 (2015): 759-771; Abudayyeh, Omar O., et al. "C2c2 is a single-component programmable RNA-guided RNA-targeting CRISPR effector." *Science* (2016): aaf5573. Nucleic acid-guided nucleic acid binding proteins, such as Argonaute and C2c2, can provide even greater flexibility as a single protein is capable of binding a diverse array of targets using a guide nucleic acid to confer specificity. These affinity-binding reactions can be used to localize a barcode nucleic acid to a target RNA molecule, such as an initiator of hybridization chain reaction (HCR), linear or circular DNA label for rolling circle amplification (RCA), or other type of detectable label. In the case of the nucleic acid-guided nucleic acid binding proteins, the guide strand of RNA or DNA could be detected instead of the target nucleic acid molecule. The guide nucleic acid molecules may be synthesized and amplified from a microarray.

Proteins which catalyze reactions of nucleic acids may be used to affect certain species of RNA or cDNA. For example, nucleic acid cleavage and/or ligation reactions may be used to modify certain RNA or cDNA species for detection in situ. An RNA or cDNA molecule can serve as a template for "Tagmentation", wherein the molecule is cleaved and an exogenous nucleic acid is ligated onto one of the fragments. See e.g., Syed, Fraz. "Second-Generation Sequencing Library Preparation: In Vitro Tagmentation via Transposome Insertion." *Tag-Based Next Generation Sequencing:* 311-321. The nucleic acid reactions can be directed to certain species using the binding specificity of the probe complex, comprising the protein component and/or a "guide" nucleic acid component. In some embodiments, certain species of RNA or cDNA which are not targets of interest can be modified using the strategies described herein in order to be eliminated for detection. For example, unwanted targets can be degraded by various exonucleases or endonucleases, such as RNase H. In some embodiments, certain species of RNA or cDNA may be modified.

Formation of Linear Polymerase Colonies for Detection

In some embodiment, the probe capturing a target comprises a common adaptor region for further amplification. In some embodiment, the probe or circularized probe can be amplified by RCA. In some embodiments, a linear amplification product can be prepared, such as polony.

As an alternative to rolling circle amplification (RCA), linear polymerase colonies ("polonies") may be formed using a linear substrate. Polonies may be generated as described in Mitra, Robi D., et al. "Fluorescent in situ sequencing on polymerase colonies." Analytical biochemistry 320.1 (2003): 55-65, which is incorporated by reference herein. Polonies may comprise RNA, cDNA, RNA or cDNA modified in situ by enzymes, nucleic acid probes hybridized to RNA or cDNA, or nucleic acid probes localized to a target RNA or cDNA species by a nucleic acid-protein complex, such as those listed above. Polonies may be subsequently detected via FISSEQ.

To summarize the RNA capture, in various embodiments, the disclosure provides that reverse transcription may be targeted to certain RNA species by synthesizing probes comprising reverse transcription primers comprising sequence complementary to RNA sequence, which act to specifically prime cDNA synthesis of those RNA species. These probes containing RT primers can subsequently be processed into a FISSEQ library.

In some embodiments, the disclosure provides that RNA species can be detected in situ wherein the final product of the probe is a circular DNA molecule, which acts as a template for rolling circle amplification (RCA), for detection via FISSEQ. In some embodiments, the capture probes can be linear probes, which are hybridized to a RNA or cDNA molecule and circularized by a ligase when annealed to complementary RNA or cDNA sequence. In some embodiment, the capture probes can be linear probes, which are hybridized to a RNA or cDNA molecule and circularized after endogenous RNA or cDNA sequence is used as a sequence template, filling in a "gap" in the linear probe, as by a reverse transcriptase, DNA polymerase, or ligase, such that the probe may be ligated into a circle. In some embodiments, the capture probes can be linear probes, which are hybridized to a RNA or cDNA molecule and circularized by a ligase using an additional "splint" oligonucleotide independent of the target RNA or cDNA molecule. In some embodiments, the capture probes can be circular probes, which are hybridized to a RNA or cDNA molecule.

In some embodiments, the present disclosure provides methods to capture a RNA target by a probe complex comprising a protein component and a nucleic acid component. The disclosure provides that RNA species can be detected in situ wherein a nucleic acid-protein complex is directed to a certain RNA or cDNA species via the binding properties of the protein, such as concatamers of engineered Pumilio homology domains, localizing a nucleic acid label to the target RNA or cDNA species. In some embodiment, the nucleic acid component of the probe complex is formed by mRNA display, ribosome display, reverse transcription and subsequent coupling of the cDNA to the protein, or other forms of linkages between a nucleic acid and protein. In some embodiments, the protein component of the probe complex is expressed from DNA or mRNA synthesized in part or full using DNA microarray technology. In some embodiment, the nucleic acid component of the probe complex is synthesized in part or full using DNA microarray technology. In some embodiments, both the nucleic acid component and the protein component of the probe complex are synthesized in part or full using DNA microarray technology. For example, the probe complex can be labeled by mRNA display, wherein an mRNA synthesized in part or in full using DNA microarray technology can direct the protein synthesis and constitute the nucleic acid label.

The disclosure provides that RNA species can be detected in situ wherein a protein or nucleic acid-protein complex is directed to certain RNA or cDNA species via the nucleic acid sequence (the "guide" nucleic acid). Exemplary nucleic acid-guided binding proteins included, but are not limited to, Argonaute, Cas9, and C2c2. In some embodiments, the nucleic acid component of a probe is directed to the target RNA or cDNA by the protein (e.g., using a nucleic acid tagged protein). In some embodiments, the nucleic acid component of the probe is added to the targeting portion of the "guide" nucleic acid, or constitutes the "guide" nucleic acid. In some embodiments, the nucleic acid component of the probe comprises a linear DNA, which is circularized as a template for rolling circle amplification (RCA). In some embodiments, the nucleic acid component of the probe comprises a linear RNA, which is specifically captured using the methods described herein, or non-specifically captured using random capture FISSEQ (e.g. Lee et al., Science 2014). In some embodiments, the nucleic acid component of the probe comprises a circular DNA, which can be amplified using RCA. In some embodiments, the nucleic acid component of the probe comprises DNA or RNA, which serves as a detectable label by in situ hybridization (ISH, fluorescent in situ hybridization (FISH), hybridization chain reaction (HCR), or cyclic hybridization chain reaction (CHCR).

The disclosure provides that RNA species can be detected in situ wherein one or more nucleic acid reactions are directed to one or more RNA or cDNA species, including cleavage, ligation, modification, such as end modifications (e.g. 5' phosphorylation), and protection. In some embodiment, the reaction is directed to certain RNA or cDNA species by the binding specificity of the probe complex, comprising the protein component and/or a "guide" nucleic acid component. In some embodiment, one or more components of the complex are synthesized using DNA microarray. In some embodiment, the target RNA or cDNA sequences are subsequently processed into a FISSEQ template for detection via sequencing.

In some embodiment, the disclosure provides that RNA species can be detected in situ wherein a linear polymerase colony (polony) is formed and detected.

In various embodiments, the target molecule is a cDNA molecule synthesized from an RNA molecule in situ, wherein the cDNA molecule may be reverse transcribed using targeted RT primers, such as those complementary to certain RNA species, or untargeted (random) RT primers, such as random hexamers or poly(dT) primers.

In various embodiments, the nucleic acid probes or nucleic acid components of the probe complex are synthesized in part or in full using DNA microarray synthesis technology. In some embodiment, the probes or the nucleic acid components of the probes can be amplified and subsequently "matured" into functional probes using methods described herein.

In some embodiment, the nucleic acid probes or nucleic acid components of the probe complexes comprise locked nucleic acid (LNA) bases or other nucleic acid analogs. In some embodiments, the modified nucleic acid probes can function to enhance the kinetics, efficiency, or specificity of hybridization or direction of the probe-target molecule interaction; e.g. by incorporation of LNA or nucleic acid analog bases by PCR, RT, or during the enzymatic amplification and "maturation" of the probe.

In various embodiments, a plurality of probes for targeted FISSEQ are synthesized and/or used simultaneously.

Various methods can be used to detect nucleic acid sequences. In some embodiments, detection of the RNA species is enabled by detection of nucleic acid sequence templated from RNA or cDNA by sequencing by synthesis (SBS), sequencing by ligation (SBL), or sequencing by hybridization (SBH). In some embodiments, the detection of targeted RNA species is enabled by the detection of nucleic acid sequence contained in the probe or nucleic acid component of the probe complex by sequencing by synthesis (SBS), sequencing by ligation (SBL), or sequencing by hybridization (SBH); e.g. "barcode" sequencing. In some other embodiments, the detection of the targeted RNA species comprises detection of both nucleic acid sequence templated from RNA or cDNA and nucleic acid sequence contained in the probe or nucleic acid component of the probe complex, sequencing by synthesis (SBS), sequencing by ligation (SBL), or sequencing by hybridization (SBH).

The disclosure provides that RNA species can be detected in situ wherein one or more nucleic acid reactions are directed to one or more RNA or cDNA species, including degradation, modification, such as end modifications (e.g. 2'O-methyl addition), and de-protection. In some embodiments, the reaction is directed to certain RNA or cDNA species by the binding specificity of the probe complex, comprising nucleic acid component synthesized using DNA microarray. In some embodiments, unwanted target RNA or cDNA sequences are subsequently depleted from the sample, such that they are not represented in the subsequent FISSEQ library and the datasets. In some embodiments, the specific depletion is mediated by RNase H digestion of an RNA:DNA hybrid duplex. In some embodiments, the specific depletion is mediated by Cas9 or other protein-nucleic acid complex. In some embodiments, the RNA species targeted for selective degradation comprise ribosomal RNA (rRNA) or transfer RNA (tRNA). In some embodiments, oligonucleotides can be used to block extension of a reverse transcriptase. In some embodiment, oligonucleotides can be used to block access to the unwanted target RNA by another RNA probe complex. Exemplary RNA species targeted for selective degradation can comprise housekeeping genes. Housekeeping genes may be constitutive genes that are required for the maintenance of basic cellular function. In some embodiments, the unwanted target RNA species targeted for selective degradation comprise genes expressed at an average RNA abundance greater than a certain level. Optionally, unwanted target RNA species targeted for selective degradation may comprise genes expressed at an average RNA abundance equal to or greater than about 100 RNA molecules per cell, 200 RNA molecules per cell, 400 RNA molecules per cell, 600 RNA molecules per cell, 800 RNA molecules per cell, 1000 RNA molecules per cell, 1200 RNA molecules per cell, 1400 RNA molecules per cell, 1600 RNA molecules per cell, 1800 RNA molecules per cell, 2000 RNA molecules per cell, 10000 RNA molecules per cell or more (e.g., where rRNA is present at up to 10 million copies per cell), or any value therebetween.

Targeted DNA Capture

All methods described in the previous section "Targeted RNA Capture" may be applied to the detection of specific DNA sequences in situ, with reasonable substitution of "RNA" or "cDNA" by "DNA", and concomitant exchange, where appropriate, of relevant enzyme or protein components of the detection scheme for corresponding enzymes or proteins which catalyze the corresponding reactions for DNA substrates.

These methods may accompany additional sample treatment steps, such as denaturing dsDNA into ssDNA for the purpose of enabling hybridization of a nucleic acid probe or nucleic acid-protein probe complex.

Capture by circularization methods may enable detection of single probes, corresponding to tens of genomic bases, which can be highly amplified using RCA. The large size of the RCA amplicon, typically a few hundred nanometers, may reduce the spatial resolution, which can be imaged using super-resolution microscopy techniques. Capture by circularization may in some instances enable detection of single nucleotide variation for mutation detection and haplotyping at arbitrary scales.

The methods described herein for using nucleic acid binding proteins to detect RNA could also be used to detect DNA. Programmable DNA binding proteins include, but are not limited to, meganucleases, zinc fingers, transcription activator-like effectors, and BurrH. Nucleic acid-guided nucleic acid binding proteins, such as Argonaute, Cas9, Cpf1, and C2c2, may in some instances provide greater flexibility as a single protein is capable of binding a diverse array of targets using a guide nucleic acid to confer specificity. In some instances, as the protein may change the energy landscape of binding (e.g., as compared to nucleic acid hybridization alone), these methods can have faster kinetics and greater sensitivity to sequence mismatches.

The most information-rich method of genomic FISSEQ is the direct analog of next generation sequencing (NGS)—using genomic sequence to template the construction of a sequencing library. Preparation of genomic sequencing libraries for NGS may involve the steps of fragmentation, end-repair, adaptor ligation, and/or PCR. However, some of these steps can be achieved simultaneously (e.g., as with Illumina's Nextera method), by using a transposase enzyme to fragment the DNA and ligate adaptors in a single reaction called "tagmentation". Existing NGS RNA-seq protocols can be adapted with modifications to RNA FISSEQ and genomic FISSEQ.

In some instances, enzymatic and/or chemical means of genomic fragmentation can be compatible with FISSEQ. Optionally, physical methods of fragmenting DNA may not be compatible with FISSEQ. The physical methods may include acoustic shearing and sonication, which may damage other aspects of the sample. DNase I or Fragmentase, a two enzyme mix (New England Biolabs) may in some instances be effective for NGS library construction. Within fixed biological specimens, DNA may also naturally fragmented by a number of factors, including decomposition of apurinic/apyrimidinic sites formed by low pH formalin and environmental conditions during storage. The ends of DNA fragments can be conditioned for adaptor ligation using a number of enzymatic treatments, including blunt-ending and 5' phosphorylation by T4 polynucleotide kinase, T4 DNA polymerase, and Klenow Large Fragment, and 3' A-tailing by Taq polymerase or Klenow Fragment (exo-).

In contrast to most genomic NGS libraries, preparative PCR to amplify the library may not be necessary. As a result, each sequence that can be detected may correspond 1:1 with a genomic fragment, avoiding the need for unique molecular identifiers or other techniques to disambiguate PCR clones. Instead, the sequencing templates for amplification by RCA can be circularized. If the fragments are modified on both ends with known adaptor sequences, the molecules can be circularized using splint ligation. Alternatively, new adaptor ligation and circularization strategies specifically tailored to FISSEQ can be devised. For example, library construction protocols involving hairpin ligation as a mechanism of circularization can be imagined. For example, hairpin nucleic acid molecules may be ligated to both strands at each end of a dsDNA fragment, serving to circularize the fragment as a template for RCA.

A strategy based on Illumina's Nextera method can be used, but using Cas9 instead of a DNA transposase to target the library construction to particular genomic sequences. This may allow finely tailoring the fragment size for library construction, as well as to enrich for loci of interest. Using this method, the Cas9 sensitivity to nucleosomes may also provide additional information about chromatin state. Detection of methylation can also be performed. For example, fragmentation by restriction enzymes sensitive to CpG methylation, a form of in situ methylation sensitive restriction enzyme sequencing (MRE-seq), can be used. BS-seq and MethylC-seq can also be adapted to FISSEQ, which use sodium bisulfite treatment to convert unmethylated cytosine to uracil, while methylated cytosine's are protected, with changes detected relative to the reference genome sequence.

To summarize targeted DNA FISSEQ, in various embodiments, the disclosure provides that DNA species can be detected in situ. In some embodiments, the final product of the probe for DNA FISSEQ is a circular DNA molecule, which acts as a template for rolling circle amplification (RCA), for detection via FISSEQ. In some embodiments, the probes for DNA target capture are linear probes, which are hybridized to a DNA molecule and circularized by a ligase when annealed to complementary DNA sequence. In some embodiments, the probes for DNA target capture are linear probes, which are hybridized to a DNA molecule and circularized after endogenous DNA sequence is used as a sequence template, filling in a "gap" in the linear probe, as by a DNA polymerase, or ligase, such that the probe may be ligated into a circle. In some embodiments, the probe for DNA target capture are linear probes, which are hybridized to a DNA molecule and circularized by a ligase using an additional "splint" oligonucleotide independent of the target DNA molecule. In some embodiments, the probes for DNA target capture are circular probes, which are hybridized to a DNA molecule.

In some embodiments, a nucleic acid-protein complex is directed to a certain DNA species via the binding properties of the protein, such as concatamers of engineered Pumilio homology domains, localizing a nucleic acid label to the target DNA species. In some embodiments, the nucleic acid component of the probe complex is formed by mRNA display, ribosome display, reverse transcription and subsequent coupling of the cDNA to the protein, or other forms of linkages between a nucleic acid and protein. In some embodiments, the protein component of the probe complex is expressed from DNA or mRNA synthesized in part or full using DNA microarray technology. In some embodiments, the nucleic acid component of the probe complex is synthesized in part or full using DNA microarray technology. In some embodiments, both a nucleic acid component and protein component of the probe complex are synthesized in part or full using DNA microarray technology, e.g. as by labeling of the complex by mRNA display. In some embodiments, the probe complex can be labeled with an mRNA, wherein the mRNA synthesized in part or in full using DNA microarray technology directs both the protein synthesis and constitutes the nucleic acid component of the probe.

The disclosure provides that DNA species can be detected in situ wherein a protein or nucleic acid-protein complex is directed to certain DNA species via the nucleic acid sequence (the "guide" nucleic acid), such as Argonaute, Cas9, and C2c2. In some embodiments, a nucleic acid component of a probe is directed to the target DNA by the protein (e.g., using a nucleic acid tagged protein). In some embodiments, the nucleic acid component of a probe is added to the targeting portion of the "guide" nucleic acid, or constitutes the "guide" nucleic acid. In some embodiments, the nucleic acid component of the probe comprises a linear DNA, wherein the linear DNA is circularized as a template for rolling circle amplification (RCA). In some embodiments, the nucleic acid component of the probe comprises a linear RNA, wherein the linear RNA is specifically captured using the methods described herein, or non-specifically captured using random capture FISSEQ (e.g. Lee et al., Science 2014). In some embodiments, the nucleic acid component of the probe comprises a circular DNA, which is amplified using RCA. In some embodiments, the nucleic acid component of the probe comprises a DNA or RNA, wherein the DNA or RNA serves as a detectable label by in situ hybridization (ISH), fluorescent in situ hybridization (FISH), hybridization chain reaction (HCR), or cyclic hybridization chain reaction (CHCR).

In various embodiments, the present disclosure provides methods of forming an in situ DNA sequencing library (FISSEQ library) by contacting the sample with a plurality of probe complexes. In some embodiments, the probe complex comprises a ssDNA, dsDNA, ssRNA, or other nucleic acid. In some embodiments, the probe complex comprises a DNA transposase. In some embodiments, the probe complex comprises a Cas9 or other nucleic acid-directed nucleic acid-binding protein.

The disclosure provides that DNA species can be detected in situ wherein one or more nucleic acid reactions are directed to one or more DNA species, including cleavage, ligation, modification, such as end modifications (e.g. 5' phosphorylation), and protection. In some embodiments, the reaction is directed to certain DNA species by the binding specificity of the probe complex, comprising the protein component and/or a "guide" nucleic acid component. In some embodiments, one or more components of the complex is synthesized using DNA microarray. In some embodiments, the target DNA sequences are subsequently processed into a FISSEQ template for detection via sequencing. In some embodiments, a linear polymerase colony (polony) is formed and detected in the target FISSEQ.

The probes disclosed herein can be synthesized by microarray. In some embodiments, the nucleic acid probes or nucleic acid components of the probe complex are synthesized in part or full using DNA microarray synthesis technology. In some embodiments, the synthesized probes can be amplified and subsequently "matured" into functional probes using methods described herein.

In some embodiments, a target dsDNA is converted into a single-stranded (ssDNA) target, as by thermal melting of the duplex and/or enzymatic digestion of one strand.

In some embodiments, the nucleic acid probes or probe complexes comprise one or more nucleotide analogs. In some embodiments, the nucleic acid probes or nucleic acid components of the probe complex comprises locked nucleic acid (LNA) bases or other nucleic acid analogs. In some embodiments, the modified probes can function to enhance the kinetics, efficiency, or specificity of hybridization or direction of the probe-target molecule interaction. The incorporation of LNA or nucleic acid analog bases can be done, for example, by PCR, RT, or during the enzymatic amplification and "maturation" of the probe.

In some embodiments, a plurality of probes are synthesized and/or used simultaneously. In some embodiments, the detection of the DNA species is enabled by detection of nucleic acid sequence templated from DNA by sequencing by synthesis (SBS), sequencing by ligation (SBL), or sequencing by hybridization (SBH). In some embodiments, the detection of the DNA species comprises detection of nucleic acid sequence contained in the probe or nucleic acid component of the probe complex by sequencing by synthesis (SBS), sequencing by ligation (SBL), or sequencing by hybridization (SBH); e.g. "barcode" sequencing. In some embodiments, the detection of the DNA species comprises detection of both nucleic acid sequence templated from DNA and nucleic acid sequence contained in the probe or nucleic acid component of the probe complex, by sequencing by synthesis (SBS), sequencing by ligation (SBL), or sequencing by hybridization (SBH).

The disclosure provides that DNA species can be detected in situ wherein one or more nucleic acid reactions are directed to one or more DNA species, including degradation, modification, such as end modifications (e.g. 2'O-methyl addition), and de-protection. In some embodiments, the reaction is directed to certain DNA species by the binding specificity of the probe complex, comprising nucleic acid component synthesized using DNA microarray. In some embodiments, the target DNA sequences are subsequently depleted from the sample, such that they are not represented in the subsequent FISSEQ library and datasets. In some embodiments, the specific depletion is mediated by RNase H digestion of an RNA:DNA hybrid duplex. In some embodiments, the specific depletion is mediated by Cas9 or other protein-nucleic acid complex. In some embodiments, the DNA species targeted for selective degradation comprise repetitive sequences. In some embodiments, oligonucleotides can be used to block extension of a DNA polymerase or the reaction of a DNA ligase. In some embodiments, oligonucleotides can be used to block access to the target DNA by another probe complex.

Enhancing Hybridization for Capture

During investigation of the strategies for targeted RNA FISSEQ and genome FISSEQ, a problem can be present: unacceptably slow kinetics of the hybridization reaction between the probe and the target molecule within a biological sample. For example, the present disclosure provides a method for enhancing a hybridization reaction in a cell or cellular matrix. In some embodiments, a crowding agent may be used to enhance hybridization for capture. In some embodiments, a crowding agent can be used, wherein the crowding agent enhances enzyme activity. In some embodiments, a crowding agent comprises a cleavable charged group, wherein the charged group can be cleaved off and washed away. In some embodiments, a crowding agent comprises a charged group, wherein the charged group can be neutralized after nucleic acid hybridization but before enzymatic reactions. In some embodiments, a crowding agent can be degraded.

Reaction Buffer
Concentration Dependency

First, all of the designs for massively multiplex targeted FISSEQ involve using a complex pool of oligonucleotide probes. However, since hybridization is a bimolecular reaction, the kinetics of hybridization may be dependent on the concentration of both molecular species. When using a pool of probes (also known as a library), the concentration of each individual probe is reduced proportional to the diversity of the library. Therefore if we attempt to simultaneously target 1000 genes, the concentration of each probe may be reduced by at least 1000-fold, and potentially more (e.g., if multiple probes are used per gene).

For this reason, execution of massively multiplex targeted FISSEQ may be enhanced by overall increasing the concentration of the probe pool. A typical probe concentration for RNA FISH may be 1~150 nM. See e.g., Raj, Arjun, et al. "Imaging individual mRNA molecules using multiple singly labeled probes." Nature methods 5.10 (2008): 877. For ISH of a complex library of probes, the concentration is scaled to up. See e.g., Chen, Kok Hao, et al. "Spatially resolved, highly multiplexed RNA profiling in single cells." *Science* 348.6233 (2015): aaa6090. In some instances, the concentration of the complex library of probes may be scaled to a concentration equal to or greater than about 10 µM, 20 µM, 40 µM, 60 µM, 80 µM, 100 µM, 120 µM, 140 µM, 160 µM, 180 µM, 200 µM, or any value therebetween. This can be further scaled. For example, the value may be further scaled by a factor of about 2, 4, 6, 8, 10, 15, 20, 25, 30, 40, 50, 60, 70, 80, 90, 100, 120, 140, 160, 180, 200, or any value therebetween. Optionally, the value may be scaled 100-fold, which may be near the solubility limit of DNA in water, ~10 mM. Relatively cheap enzymatic amplification of microarray-synthesized oligonucleotide libraries make this within the realm of possibility.

Crowding Agents with Enhanced Enzyme Compatibility

Optimal conditions for efficient probe hybridization and the downstream enzymatic reactions may tend to be generally mutually exclusive in some instances. For example, in situ hybridization may be efficient in the presence of a crowding agent. An example of a crowding agent may be dextran sulfate. However, enzymes may be strongly inhibited by dextran sulfate. See e.g., Bouche, J. P. "The effect of spermidine on endonuclease inhibition by agarose contaminants." *Analytical biochemistry* 115.1 (1981): 42-45. Being a highly charged, high molecular weight polymer, it may be difficult to wash dextran sulfate from the sample to the point where the downstream enzymatic reactions, e.g., reverse transcription, ligation, DNA polymerization, are not strongly inhibited. In the absence of a crowding agent, however, the kinetics of in situ hybridization may be orders of magnitude slower. See e.g., Wahl, Geoffrey M., Michael Stern, and George R. Stark. "Efficient transfer of large DNA fragments from agarose gels to diazobenzyloxymethyl-paper and rapid hybridization by using dextran sulfate." *Proceedings of the National Academy of Sciences* 76.8 (1979): 3683-3687. Therefore, a crowding agent that does not strongly inhibit enzymatic reactions can be used in FISSEQ. Crowding agents may be typically high-molecular weight, high valency charged polymers. For example, crowding agents may be polymers such as polyacrylic acid, polyvinylsulfonic acid, and alginate. Optionally, crowding agents may be polymers similar to dextran sulfate. In some instances, an intermolecular organization of the crowding agents may be a factor in determining its effectiveness as a crowding agent.

As one example, dextran sulfate is understood to aid in the formation of networks (highly localized concentrations of probes) during hybridization, thus expediting the annealing process. The G-blocks of alginate are believed to participate in intermolecular cross-linking with divalent cations (e.g., $Ca^{2+}$) to form hydrogels. Dextran sulfate is not known to form hydrogels, other than under exogenous chemical cross-linking reactions and in the presence of chitosan, neither of which is present during typical nucleic acid hybridization reactions. In some instances, the crowding agent may comprise an ability to self-associate in the formation of hydrogels. Alternatively, the crowding agent may not comprise the ability to self-associate in the formation of hydrogels. Optionally, this difference in the ability to self-associate in the formation of hydrogels may explain the difference between dextran sulfate and alginate in improving the kinetics of nucleic acid DNA hybridization reactions.

For example, polyacrylic acid and polyvinylsulfonic acid may both effectively function as a crowding agent while alginate may not. This may be due to the intermolecular organization, which reduces its effectiveness in crowding DNA. In some instances, polyacrylic acid strongly may inhibit enzymatic reactions, but polyvinylsulfonic acid may exhibit much less inhibition. As one example, one mechanism of inhibition may be via chelation of essential metal or charged cofactors, such as $Mg^{2+}$, $Ca^{2+}$, $Mn^{2+}$, $Na^+$, phosphate, and other metal and charged ions, which are required for enzyme function. A polyion salt such as sodium polyacrylic acid may exchange sodium ions for magnesium ions in the presence of a magnesium-containing enzyme reaction buffer, reducing the effective concentration of the essential cofactor. Another mechanism of inhibition may be binding and structural damage to the enzyme, e.g. the charge attraction and binding between charged domains of the enzyme and the ionic polymer, which may cause effective sequestration of the enzyme within the reaction, as well as disrupt electrostatic or charge interactions within the enzyme, which are required for enzyme structure and related function. Wettability, or hydrophobicity, charge, and structure may alternatively, or additionally contribute to the strength of polyion-protein interactions. Protein absorption on the polyion or within the polyionic network may contribute to effective decrease in enzyme concentration.

In some embodiments, compounds that can function as crowding agents, but have some property of molecular programmability may be used. For example, some polymers that can function as crowding agents can be used and subsequently the charged group can be cleaved off or neutralized. This can convert the compound into a neutral polymer like PEG, which actually enhances the efficiency of enzymatic reactions. In some embodiments, polymers can function as a crowding agent, and then be specifically degraded into small monomers and can be easily washed from the sample. The chemistry of passivation or degradation of the crowding agent needs to be orthogonal to nucleic acids, i.e., not degrading nucleic acids or rendering nucleic acids incompatible. Some of these functional groups include alpha-hydroxy acids, which can be cleaved by sodium periodate; beta-keto acids, which can be cleaved with heat; phosphorothioate linkages, which can be cleaved with silver ions; disulfide linkages, which can be cleaved by reduction into thiols; and other types of chemical linkages which may be cleaved by photo- or chemical treatment.

Examples of programmable polyions or polyelectrolytes for enzyme-compatible enhancement of nucleic acid hybridization kinetics include polycondensation reactions of Cys (Lys)nCys, polymers such as PEG, PVA, or PAA, which may be subsequently modified via a cleavable linker to include chemical groups conferring ionic charge, or polymers formed from monomers including cleavable linkages, such that the polymer may be degraded subsequent to functioning as a crowding agent. See e.g., Oupický, David, Alan L. Parker, and Leonard W. Seymour. "Laterally stabilized complexes of DNA with linear reducible polycations: strategy for triggered intracellular activation of DNA delivery vectors." *Journal of the American Chemical Society* 124.1 (2002): 8-9. As an alternative to ionic charge, these polymers may include non-ionic groups that become hydrated in solution, which also enhance nucleic acid hybridization rates by molecular crowding and/or sequestration of water.

In various embodiments, the disclosure provides methods to enhance the hybridization of diverse libraries of probes for targeting the capture of RNA, cDNA, and DNA species for detection via FISSEQ. In some embodiments, the method comprises adding a crowding agent in the hybridization buffer. In some embodiments, a hybridization buffer containing high salt, such as SSC (sodium chloride sodium citrate buffer), can be used. The salt concentration can be at 1×, 2×, 5×, 10×, or more concentrations. In some other embodiments, the salt concentration can be at from about 1× to 3×, from about 3× to 5×, or from about 5× to 10×. In some embodiments, a hybridization buffer containing blocking agents can be used. The blocking agents can reduce non-specific binding of probes to off-target sequences and/or by preventing electrostatic interactions with other components of the sample, such as yeast tRNA, salmon sperm, detergents such as Triton-X, Tween 20, SPAN, peptides such as BSA, and other agents such as Ficoll. In some embodiments, a hybridization buffer containing agents which alter the annealing properties of DNA, such as the melting temperature. Exemplary agents that can alter the annealing temperature include formamide. In some embodiments, high concentrations of probe can be used. Exemplary concentrations of probes can include 1-150 nM, 1-150 µM, or up to 10 mM. In some embodiments, a crowding agent, such as dextran sulfate or polyacrylic acid, can be used. In some embodiments, a crowding agent can have average molecular weights Mn of 1-10 kDa, 10-20 kDa, 10-100 kDa, 100-300 kDa, or 100-1000 kDa. In some embodiments, a crowding agent can have a charge density of 1-10%, 10-30%, 10-99%, or 100% monomer occupancy. In some embodiments, a crowding agent can present in 1%, 5%, 10%, 15%, 20%, or more weight per volume in the reaction.

The disclosure provides a crowding agent, for example, a polyionic, polyelectrolyte, or hydrophilic and strongly hydrating polymer, comprising a polymer backbone and one or more hydrating groups. The hydrating groups can be ionic, electrolytic, or hyrophylic. In some embodiments, the hydrating groups may be specifically inactivated, e.g., as by rendering an ionic group to have neutral charge, or as by rendering a strongly hydrating group to be weakly hydrating;

In some embodiments, the inactivation chemistry is substantially nonreactive with RNA, DNA, proteins, and/or other types of biomolecules. In some embodiments, the inactivated polymer is compatible with enzymatic reactions.

The disclosure provides a crowding agent, for example a polyionic, polyelectrolyte, or hydrophilic and strongly hydrating polymer, comprising a cleavable linkage between the polymer backbone and the hydrating group. In some embodiments, the cleavable linkages comprise alpha-hydroxy acids, which can be cleaved by sodium periodate. In some embodiments, the cleavable linkages comprise beta-keto acids, which can be cleaved with heat. In some embodiments, the cleavable linkages comprise phosphorothioate linkages, which can be cleaved with silver ions. In some embodiments, the cleavable linkages comprise disulfide linkages, which can be cleaved by reduction into thiols. Other types of chemical linkages may be cleaved by photo- or chemical treatment.

The disclosure provides a crowding agent, for example a polyionic, polyelectrolyte, or hydrophilic and strongly hydrating polymer, comprising cleavable linkages along the backbone of the polymer, wherein cleavable linkages include those disclosed herein.

The disclosure provides use of a crowding agent for targeted RNA or DNA detection, wherein a plurality of probes is hybridized in situ using a hybridization buffer containing one of the crowding agents disclosed herein.

The disclosure provides a method of detecting RNA and DNA, comprising the step of hybridizing a plurality of probes in situ using a hybridization buffer containing one of the crowding agents disclosed herein. In some embodiments, the methods further comprise the step of triggering cleavage of the cleavable groups present in the crowding agent.

The disclosure provides a method of detecting RNA and DNA, comprising the step of hybridizing a plurality of probes in situ using a hybridization buffer containing one of the crowding agents disclosed herein and further comprising the step of inactivating the hydrating groups.

DNA Array Synthesis of Probe Pools

A DNA microarray (also commonly known as an array, DNA chip, biochip, or chip) may refer to a collection of microscopic DNA spots attached to a solid surface. See e.g., Heller, Michael J. "DNA microarray technology: devices, systems, and applications." *Annual review of biomedical engineering* 4.1 (2002): 129-153. Microarray DNA synthesis platforms, offered commercially by Agilent, CustomArray, and Twist Bioscience, may in some instances be used to generate massively complex short (approximately 200 nucleotide) oligonucleotide libraries. See e.g., Kosuri, Sriram, and George M. Church. "Large-scale de novo DNA synthesis: technologies and applications." *Nature methods* 11.5 (2014): 499-507. Microarray synthesis may refer to the synthesis of DNA or nucleic acid analog oligonucleotides attached to a solid substrate. Commercial supplier Twist Bioscience, for example, features microarrays containing 9,600 wells with 121 discrete oligonucleotide species synthesized per well, for a total of 1.16 million oligonucleotides per array. Commercial supplier Agilent's OLS libraries contain just over 244,000 oligonucleotide species, while the DNA microarray of commercial supplier Custom Array synthesizes just over 94,000. Each DNA species may be synthesized in minute quantities, such as picomoles (10-12 moles) of DNA molecules. Each DNA microarray synthesis technology may vary in features such as error rate, oligonucleotide length, and sequence limitations such as homopolymer repeats and secondary structure. These libraries of oligonucleotides may be typically liberated from the solid support substrate into a solution of DNA species representing a renewable source of single-stranded DNA probes, generating using techniques to highly amplify and process the library, in whole or in specific subpools. See e.g., Beliveau, Brian J., Nicholas Apostolopoulos, and Chao-ting Wu. "Visualizing genomes with Oligopaint FISH probes." *Current Protocols in Molecular Biology* (2014): 14-23; Chen, Kok Hao, et al. "Spatially resolved, highly multiplexed RNA profiling in single cells." *Science* 348.6233 (2015): aaa6090; Kosuri, Sriram, et al. "Scalable gene synthesis by selective amplification of DNA pools from high-fidelity microchips." *Nature biotechnology* 28.12 (2010): 1295-1299. Alternatively, the oligonucleotides may be amplified directly from the solid support, in whole or in specific subpools.

Computational Design

Unlike traditional DNA synthesis, for which sequences can be designed manually or individually using computational tools, the scale of array DNA synthesis can be designed with computational pipelines for sequence design and management. See e.g., Rozen, Steve, and Helen Skaletsky. "Primer3 on the WWW for general users and for biologist programmers." *Bioinformatics methods and protocols* (1999): 365-386; Rouillard, Jean-Marie, Michael Zuker, and Erdogan Gulari. "OligoArray 2.0: design of oligonucleotide probes for DNA microarrays using a thermodynamic approach." *Nucleic acids research* 31.12 (2003): 3057-3062). These methods may consider both aspects of probe design related to the function of the probes as well as idiosyncrasies of the array manufacturing process.

DNA Probes

For designing probes complementary to genomic sequences or RNA sequences derived from the genome, a custom Genome Tools Python library can be used to memory map the chromosomal sequence files and provide annotation-derived indexing. This approach may enable lazy-loading of chromosomal regions of interest while minimizing excessive memory use, disk thrashing, performance bottlenecks, and other downsides associated with attempting to store full chromosomal data in primary memory. When using an SSD drive, accessing sequences may be approximately 80% as fast as in memory access, but with a minimal memory footprint containing only index metadata and lazy-loaded regions of interest. The GFF/GTF File Format (General Feature Format/General Transfer Format) provided by Ensemble may be used for storing genome annotations. See e.g., Kawaji, Hideya, and Yoshihide Hayashizaki. "Genome annotation." *Bioinformatics: Data, Sequence Analysis and Evolution* (2008): 125-139. To allow facile compilation of gene target lists, the Gencode or other reference annotation and translation tables can be used to map between genomic, transcriptomic, and protein annotations. See e.g., Harrow, Jennifer, et al. "GENCODE: producing a reference annotation for ENCODE." *Genome biology* 7.1 (2006): 1. The appropriate reference genome build on a per-application basis can be selected, as individual projects and collaborators rely on build-specific datasets for design-of-experiment. In some instances, the stable GRCh37 annotation and sequence assembly release can be used.

RNA Probes

For designing probes against RNA, the fact that RNA species are present in many isoforms due to alternative splicing may be taken into consideration. If interested in detecting a particular sequence feature of the RNA, such as a particular exon, intron, sequence junctions, expressed polymorphism, or site of RNA editing, the approach may be limited to designing probes that specifically target that segment of the RNA molecule. In these cases, the Genome Tools library may be used to generate annotation-derived probe sequences, constrained by the probe sequence design logic.

In some instances, it may be desirable to detect any isoforms of an RNA species. To maximize the generality of the probes of the present disclosure across transcript isoforms, the Genome Tools library may be used to create an exon "pileup" for the target RNA species. Conceptually, the pileup may be intended to identify exonic regions that are most common across all isoforms. In practice, the pileup may simply be an array, the extents of which may be defined by the outermost bounds of the transcribed sequence (i.e., the first base of the 5'-most transcript variant and the last base of the 3'-most variant), with respect to the genome. The value at each position in the array may be the number of annotated transcript variants that have exonic sequence at the respective location among all isoforms. This method may assume that all transcript isoforms are equally likely to be expressed in any given experiment. The sequence design can be improved by incorporating prior knowledge about the tissue- and cell-type specific expression patterns of transcript isoforms to improve the fraction of probes complementary to expressed RNA sequence. There may be additional means of leveraging annotation data to provide weighted exon scoring with respect to organism-level transcript frequencies or annotation confidence.

Probe Design Logic

Given an assay, a thermodynamic target melting temperature for the probe design can be determined. The target sequences provided by Genome Tools for genomic or transcriptomic targets can be then chunked into small candidate probe sequences, such as 15 nucleotide segments. For gene-specific RT primers, the length of probes can often be a compromise between enforcing specificity and minimizing propensity for self-circularization. In some embodiments, the full "adapter-barcode-probe" construct has a length of no more than 40 nucleotides in length to minimize self-circularization. In some other embodiments, the full "adapter-barcode-probe" construct can be 10-15 nucleotides in length, 15-20 nucleotides in length, 20-25 nucleotides in length, 25-30 nucleotides in length, 30-35 nucleotides in length, 35-40 nucleotides in length, 45-50 nucleotides in length, 50-55 nucleotides in length, 55-60 nucleotides in length, 60-65 nucleotides in length, 65-70 nucleotides in length, 70-75 nucleotides in length, 75-80 nucleotides in length, 80-85 nucleotides in length, 85-90 nucleotides in length, 90-95 nucleotides in length, or 95-100 nucleotides in length. In some embodiments, the full "adaptor-barcode-probe" construct can be at least 20 nucleotides in length, at least 30 nucleotides in length, at least 40 nucleotides in length, at least 50 nucleotides in length, at least 60 nucleotides in length, at least 70 nucleotides in length, at least 80 nucleotides in length, at least 90 nucleotides in length, at least 100 nucleotides in length, or at least 1500 nucleotides in length. After the initial chunking, each candidate probe can be scored using metrics intended to predict its specificity and efficiency in the context of both the initial synthesis and FISSEQ sample preparation. For example, we exclude any segments containing G quadruplex. We then score the probe based on melting temperature, which also provides an implicit GC metric if the probe length is also pre-defined. In some embodiments, the probe length can be determined and fixed, which simplifies the array synthesis by providing that all oligonucleotides are of equal length. (It is possible to add padding sequences to the ends of oligonucleotides to enable array synthesis of libraries with variable length. However, this may complicate probe maturation and downstream processing as the final probes will also have a distribution of lengths, limiting the degree to which we can use size selection to purify the probe pool.) For RNA probes, the segments can also be scored using the exon pileup described herein.

Additional design constraints may be considered as a means of improving both individual and population-level probe performance. For example, probes may be screened to reduce the likelihood of probe heterodimerization. Finding a set of mutually compatible probe sequences within a thermodynamic threshold for heterodimer formation may be a challenging computational task. One such approach could involve generating a graph data structure describing all pairwise interactions within a given probe pool and then using a network elimination algorithm to produce a set of probe nodes with minimal or zero interconnectivity (indicating a lack of predicted heterodimization reactions). While this approach has proven effective in similar contexts (Xu, Qikai, et al. "Design of 240,000 orthogonal 25mer DNA barcode probes." *Proceedings of the National Academy of Sciences* 106.7 (2009): 2289-2294), it may be computationally infeasible for this application, as the presence of our many other constraints may preclude convergence on an acceptable solution. This effort would be enabled by better understanding of the sequence-dependency of downstream FISSEQ steps, such as RT, which would improve the metrics for network elimination.

In some instances, it may be reasonable to screen for specificity of the probe. There are a number of strategies that may be used to computationally screen probes for off-target binding. A simple strategy would be to prune common k-mers from the pool See e.g., Melsted, Pall, and Jonathan K. Pritchard. "Efficient counting of k-mers in DNA sequences using a bloom filter." *BMC bioinformatics* 12.1 (2011): 1. Thermodynamic considerations can also be used; the OligoArray software (Rouillard, Jean-Marie, Michael Zuker, and Erdogan Gulari. "OligoArray 2.0: design of oligonucleotide probes for DNA microarrays using a thermodynamic approach." Nucleic acids research 31.12 (2003): 3057-3062), for example, uses the Blast algorithm with a short word size to find all similarities. The resulting similarity matrix can be used to compute the thermodynamic values (Tm, free energy, enthalpy and entropy; using MFOLD with thermodynamic parameters from SantaLucia (Zuker, Michael. "Mfold web server for nucleic acid folding and hybridization prediction." Nucleic acids research 31.13 (2003): 3406-3415; SantaLucia, John. "A unified view of polymer, dumbbell, and oligonucleotide DNA nearest-neighbor thermodynamics." Proceedings of the National Academy of Sciences 95.4 (1998): 1460-1465)) of all possible hybridizations between the target sequence and similar sequences. Potential sequences can then be eliminated using a thermodynamic threshold for cross-hybridization. The role of sub-regions of the primer can be considered in conferring probe specificity via enzyme mismatch sensitivity profiles. For example, the 3' ends of targeted RT primers may especially be sensitive to mismatches. See e.g., Ye, Jian, et al. "Primer-BLAST: a tool to design target-specific primers for polymerase chain reaction." *BMC bioinformatics* 13.1 (2012): 1. For designing MIPs and padlock probes, the ligase can be sensitive to mismatches within approximately 6 bases on each side of the nick. See e.g., Mitra, Robi D., et al. "Fluorescent in situ sequencing on polymerase colonies." *Analytical biochemistry* 320.1 (2003): 55-65.

Furthermore, it may be reasonable to consider the sequence-dependency of downstream FISSEQ steps. For example, RNA secondary structure and the presence of polysome complex or paused ribosomes may inhibit access to the RNA by our probes. See e.g., Ståhlberg, Anders, et al. "Properties of the reverse transcription reaction in mRNA quantification." *Clinical chemistry* 50.3 (2004): 509-515. In some instances, nucleosomes may inhibit genomic access by DNA probes, as it does to Cas9. See e.g., Horlbeck, Max A., et al. "Nucleosomes impede Cas9 access to DNA in vivo and in vitro." *Elife* 5 (2016): e12677. The enzymes themselves, such as ligases, polymerases, and the reverse transcriptase may have intrinsic biases with respect to the sequence of the substrate. See e.g., Hafner, Markus, et al. "RNA-ligase-dependent biases in miRNA representation in deep-sequenced small RNA cDNA libraries." *Rna* 17.9 (2011): 1697-1712. These sequence dependencies can be measured directly from experiments using probe-level barcodes.

Barcode Assignment

Two approaches to barcode assignment can be to randomly assign barcodes from a pool of k-mers, or to assign barcodes using an iterator function to increment the barcodes. However, barcodes designed using these strategies may have limited capacity for error correction or error detection, and may generate sequences that are sub-optimal for synthesis. Instead, the assignment can be started with a large pool of barcodes, derived from the pool of k-mers and excluding homopolymer and GC runs ≥4, as well as G quadruplex. From this pool, a set of g barcodes can be identified with Hamming distance h using a graph based algorithm (Conway, Nicholas J. and Pruitt, Benjamin. "Libnano, a low-level python library for DNA sequence file io, searching, and manipulation." Unpublished GitHub Repository; Hagberg, Aric A., et al. "Exploring network structure, dynamics, and function using NetworkX." Proceedings of the 7th Python in Science Conference (SciPy2008) 11-15, Pasadena, Calif. USA). The Hamming distance may provide for detection and correction of errors in sequenced barcodes, as it can require a certain number sequencing errors to cause one barcode to be detected as another barcode. For example, using an iterator to increment barcodes might assign "AA" to the first probe, "AT" to the second, "AG" to the third, and so on. Using this strategy, a sequencing error in the second base of this dinucleotide barcode would cause one barcode to be detected as another valid barcode in the set. If the barcodes are separated by Hamming distance, most sequencing errors generate invalid barcode sequences, which can simply be mapped to the nearest valid barcode sequence. More sophisticated error correction could also use heuristics that consider error bias and base call certainty. Those probes can be paired with our constant adaptor features of the probe, such as the "T2S" (ACT TCA GCT GCC CCG GGT GAA GA) sequencing primer annealing region, also requiring the combined sequence to satisfy homopolymer restrictions and fall within homodimer and hairpin thermodynamic thresholds.

Probe Pool Selection

Having assembled the full probes, containing sequences complementary to target RNA or DNA molecules, adaptor sequences, such as T2S, and barcodes, a final screen can be performed to eliminate any probes containing homopolymer runs, or that form homodimers or hairpins given thermodynamic thresholds. For example, probes having homodimer or hairpin Tm>30° C. can be eliminated. Heterodimers or off-target interactions created during assembly of the full probe sequence can also be considered. In synthesizing probe libraries, we can be limited by the number of distinct oligonucleotide features on the microarray. When this happens, the top n probes per gene or target locus can be taken using the scoring metrics described herein.

Subpool Amplification

Given the large number of oligonucleotide features per microarray, multiple probe libraries can be synthesized on a single chip. In order to generate a single probe library, subpool amplification may be used to specifically amplify a fraction of the probe population for maturation and use in FISSEQ. See e.g., Kosuri, Sriram, et al. "Scalable gene synthesis by selective amplification of DNA pools from high-fidelity microchips." *Nature biotechnology* 28.12 (2010): 1295-1299. Even in the case where an array contains only a single library, additional PCR primer sequences can still be included, as the amount of raw material produced by the array may be on the scale of nanograms. To avoid internal mispriming from payload sequences and cross-talk during subpool amplification, primers may be automatically generated for these reactions using heuristics derived from quantitative modeling and empirical data. This method can allow incorporation of sequence features into the priming regions, such as Type IIS restriction sites, which may be used to process the library into a mature probe pool.

Probe Maturation Strategies

After collecting the DNA library from the microarray chip, an initial global or subpool amplification can be performed. For use in FISSEQ, a micrograms or even milligrams of the mature single stranded probe library can be prepared, which does not include the amplification primer sequences. There are many strategies for achieving this, for example, in vitro transcription or PCR-based methods, which are described herein. Methods to process probes are also provided herein, such as for synthesis of MIPs and padlock probes. These types of probes by design have the variable sequences on the 5' and 3' ends of the probe. Type IIS restriction enzymes can be used to cut at a defined site, which is outside of the enzyme recognition sequence. See e.g., Szybalski, Waclaw, et al. "Class-IIS restriction enzymes—a review." Gene 100 (1991): 13-26. We find that the. The efficiency of cutting can be enhanced by using a splint oligonucleotide that extends over the restriction enzyme recognition sequence, to just beyond the start of the variable sequence, using inosines or universal bases to generate a duplex 1-3 bases past the cutting site.

IVT

In vitro transcription (IVT) may be enabled by including a T7 RNA polymerase promoter site in the probe library, which is used to linearly amplify the entire probe pool into highly abundant single stranded RNA transcripts. A targeted reverse transcription can then be performed to efficiently convert the RNA molecules into single stranded cDNA, after which the RNA is degraded. See e.g., Chen, Kok Hao, et al. "Spatially resolved, highly multiplexed RNA profiling in single cells." Science 348.6233 (2015): aaa6090. The single-stranded cDNA may be further modified, as by splint restriction, wherein an oligonucleotide is annealed to the cDNA and the duplex DNA region is targeted by a restriction enzyme for digestion.

PCR

Another strategy may be to use PCR to exponentially amplify the library, followed by specific digestion of one of the duplex strands. One method for achieving this may be to include a 5' phosphate on one primer, which allows the resulting strand to be digested by lambda exonuclease. See e.g., Beliveau, Brian J., et al. "Versatile design and synthesis platform for visualizing genomes with Oligopaint FISH probes." Proceedings of the National Academy of Sciences 109.52 (2012): 21301-21306. Before or after exonuclease digestion, the probe can be further processed using restriction enzymes.

Purification and Validation

Figure 2A:
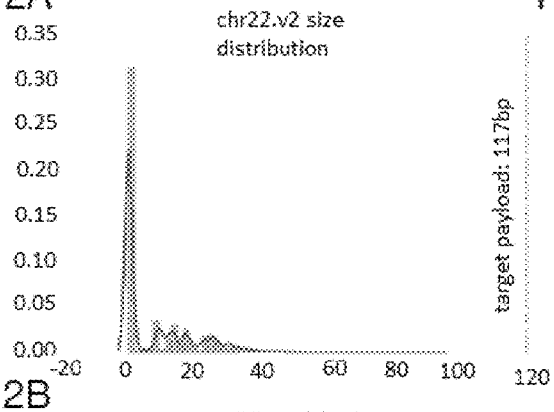
FIG. 2A illustrates an exemplary results of validation of microarray-synthesized FISSEQ primer library, in accordance with embodiments.
Figure 2B:
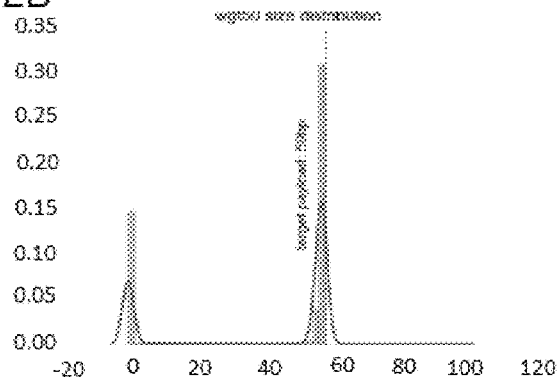
FIG. 2B illustrates that a significant fraction of the pool contains a payload that matches the expected size, which is indicated by the dotted line, in accordance with embodiments.
Figure 2C:
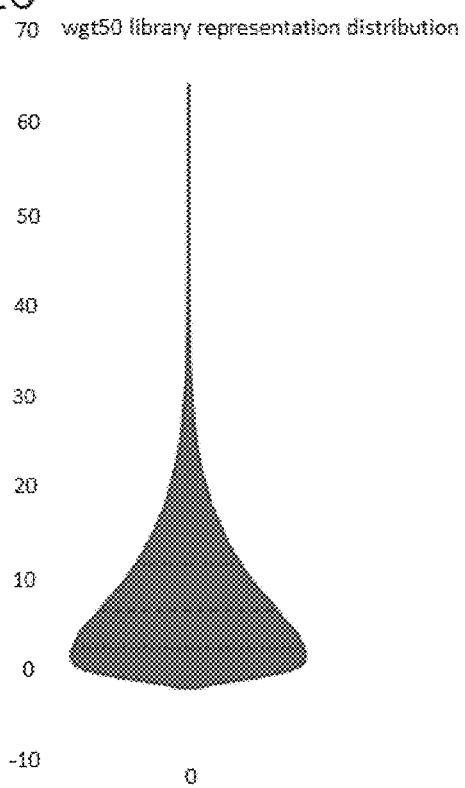
FIG. 2C illustrates a violin plot of the distribution of payloads of FIG. 2B, showing that most members of the library are present at an average of a few copies, in accordance with embodiments.

The products may also be further purified, as by ethanol precipitation, beads, or columns to remove dNTPs or other reaction products and also to desalt the oligonucleotides. The probes can also be purified using polyacrylamide gel electrophoresis (PAGE) or High Performance Liquid Chromatography (HPLC) to select only correctly-sized products. To ensure that the final library has the correct sequences, next-generation sequencing can be used to measure the distribution of payload sizes, error rates during synthesis and amplification, and sequence diversity (FIGS. 2A-2C).

The present disclosure provides methods to identify a set of target RNA and DNA sequences. In some embodiments, one or more of DNA locus can be identified. In some embodiments, one or more of DNA sequence, including DNA sequence or structural variants can be identified. In some embodiments, one or more of RNA species can be identified. In some embodiments, one or more RNA sequence, including RNA editing, splicing, expressed sequence variation can be identified.

The present disclosure provides that reference sequence databases are curated and mined to discover appropriate primer sequences for detection in situ using the methods described above, including for sequences of RT primers, PCR primers, MIP and padlock probes, Cas9 guide RNAs, and other types of targeted probes.

The disclosure provides that candidate sequences are scored using metrics intended to predict its specificity and efficiency in the context of both the initial synthesis and FISSEQ sample preparation. Exemplary metrics to be considered including sequence content, both overall, e.g. GC content, and local, e.g. G quadruplex, homopolymer runs; melting temperature and other thermodynamic properties such as free energy, enthalpy and entropy; bias of proteins and enzymes used in the probe complex, such as Cas9 and C2c2, or in downstream processing, such as the reverse transcriptase, DNA polymerase, DNA ligase, RNA ligase, Circ-ligase; secondary structure and homodimer formation; limitations or optimizations of the microarray synthesis platform; target sequence features of the RNA or DNA, including secondary structure and in situ protein occupancy (e.g., nucleosomes and ribosomes); specificity of nucleic acid hybridization relative to other sequences known to be present; and/or sequence specificity of a subset of the probe relevant to an enzymatic step, e.g., the 3' end of an RT primer, or the seed region of a microRNA.

The disclosure provides curation of a set of identifying barcode sequences, which can be detected by sequencing by synthesis (SBS), sequencing by ligation (SBL), or sequencing by hybridization (SBH), for the identification of the target molecule. In some embodiments, the curation process may consider features such as: sequence content, both overall, e.g. GC content, and local, e.g. G quadruplex, homopolymer runs; melting temperature and other thermodynamic properties such as free energy, enthalpy and entropy; bias of proteins and enzymes used in the probe complex, such as Cas9 and C2c2, or in downstream processing, such as the reverse transcriptase, DNA polymerase, DNA ligase, RNA ligase, Circ-ligase, or enzymes used for sequencing; secondary structure and homodimer formation; limitations or optimizations of the microarray synthesis platform; and error detection and error correction features, such as Hamming distance, as well as parity bits and codes constructed using algorithms such as Golay.

The disclosure provides computational design of the DNA microarray synthesis product, including the target sequences mined and scored as described above. The present disclosure also provides methods to design additional sequences including those for PCR amplification of the library; subpool amplification of a subset of the total library; probe purification; sequences enabling probe expression and maturation, e.g. the T7 RNA polymerase promoter sequence, sites for restriction enzymes, etc.; sequences relevant to FISSEQ or in situ detection, e.g., sequencing adaptors, HCR or CHCR initiators or adaptor sequences, sites of primary, secondary, or additional probing in situ; and barcoding sequences used for identification of the probe and cognate target molecule.

The disclosure provides curation of a library from the candidate sequences, and/or modified candidate sequences (e.g., after adding adaptors and other features necessary for subsequent amplification and processing, FISSEQ, identifying barcodes, etc.). In some embodiments, the methods comprise the steps of discovering a mutually compatible set of candidate sequences. In some embodiments, the methods further comprise considering heterodimerization and off-priming. In some embodiments, the methods further comprise considering sequences formed during assembly of the full sequence, such as at the junction of sequence features, e.g. the junction between a subpool amplification primer and the segment of the primer responsible for binding a target nucleic acid. In some embodiments, the methods comprise considering sequence content, both overall, e.g. GC content, and local, e.g. G quadruplex, homopolymer runs; melting temperature and other thermodynamic properties such as free energy, enthalpy and entropy; secondary structure and homodimer formation; and limitations or optimizations of the microarray synthesis platform.

The disclosure provides methods of amplifying and maturing a probe library for targeted RNA or DNA detection in situ from a DNA microarray or DNA oligonucleotides liberated from a DNA microarray. In some embodiments, the methods comprise PCR. In some embodiments, the methods comprise enzymatic processing, such as cleavage by restriction enzymes to remove PCR and other adaptor sequences which are irrelevant or deleterious to use for in situ RNA or DNA detection. In some embodiments, the methods comprise inclusion of chemical modifications, modified bases, or nucleic acid analogs during probe amplification and/or maturation. The modifications include, but are not limited to, chemical handles for cross-linking, including primary amines, biotin/streptavidin, thiol; locked nucleic acid (LNA) bases, which are known to improve hybridization kinetics and specificity; and 2'-O-methyl RNA bases and phosphorothioate linkages, which are known to make oligonucleotides resistant to certain nuclease treatments. In some embodiments, the disclosure provides methods of generating a single-stranded final product, such as by lambda exonuclease digestion of a 5' phosphate-bearing complementary strand or expression of RNA, such as by IVT, followed by RT and degradation of the RNA to form a single stranded product. In some embodiments, the present disclosure provides methods for purification, including by adding handles for purification, such as biotin, or by PAGE, HPLC, using beads, or other methods known to a skilled artisan of cleaning up and purifying oligonucleotides; and In some embodiments, the present disclosure provides methods of using next generation sequencing (NGS) to validate the product library, including determination of variation in the presence and abundance of individual probes; discovery of the relationship between identifying barcodes and the sequences relevant to molecular targeting, in the case where barcodes are synthesized randomly The disclosure provides methods for in situ targeted detection of RNA and/or DNA species, using probes synthesized by DNA microarray.

Terms and symbols of nucleic acid chemistry, biochemistry, genetics, and molecular biology used herein may follow those of standard treatises and texts in the field, e.g., Komberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Computer Control Systems

Figure 7:
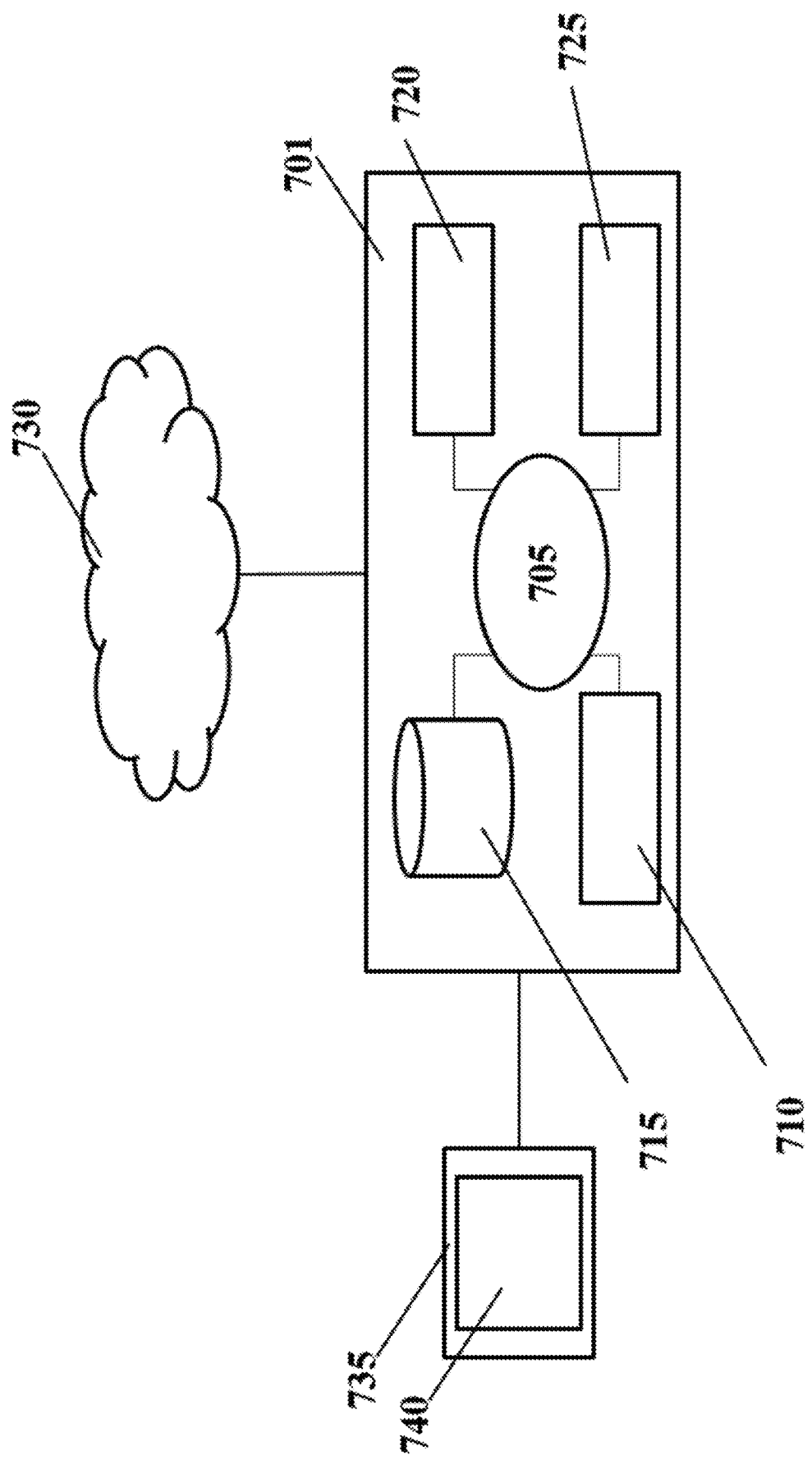
FIG. 7 shows a computer control system that is programmed or otherwise configured to implement methods provided herein.

The present disclosure provides computer control systems that are programmed to implement methods of the disclosure. FIG. 7 shows a computer system 701 that is programmed or otherwise configured to aid in generation of said libraries of probes, or sequencing nucleic acids of interest, as described here. The computer system 701 can regulate various aspects of the present disclosure, such as, for example, determination of target sequences of interest, and/or scoring of said probes. In some aspects, the computer system may be programmed to control release of reagents, activation of reactions (e.g., amplification reactions), and/or may initiate a sequencing reaction to take place. The computer system 701 can be an electronic device of a user or a computer system that is remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., a user generating said probes of the current disclosure or a user utilizing such probes). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, scoring of said probes, or showing detection and/or sequencing of biomolecules of interest using said libraries of probes. Examples of UI's include, without limitation, a graphical user interface (GUI) and web-based user interface. In some instances, the computer system may be configured to be in communication with various other devices and may be programmed to control such devices. For example, the computer system may be in communication with various light sources (e.g., fluorescent light sources) and/or platforms for utilizing said probe libraries or platforms utilized for sequencing.

Methods and systems of the present disclosure can be implemented by way of one or more algorithms. An algorithm can be implemented by way of software upon execution by the central processing unit 705. The algorithm can, for example, be executed so as to generate said probes or libraries of probes of the current disclosure. The algorithms may comprise relevant parameters for designing and/or generating said probes. In some instances, the algorithms may comprise relevant parameters to implement detection of biomolecules of interest.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

EXAMPLES

Example 1—Exemplary Probe Designs

Exemplary linear probe design is shown in FIGS. 1A-C. FIG. 1A depicts that a mature primer includes: (a) sequence complementary to the RNA molecule at the 3' end, which anneals to the RNA molecule in situ and primes RT; (b) a common adaptor sequence, from which RCA and sequencing reactions are primed; (c) a gene-level barcode at the 5' end; and 5' phosphorylation. FIG. 1B depicts that the complementary region of the primer anneals to the target RNA species and primes an RT reaction, incorporating RNA-templated bases into the cDNA. FIG. 1C depicts that in the linear RCA amplicon each of the n tandem repeats contains the barcode as well as adjacent RNA-templated sequence, enabling quantification of capture specificity.

Figure 4A:
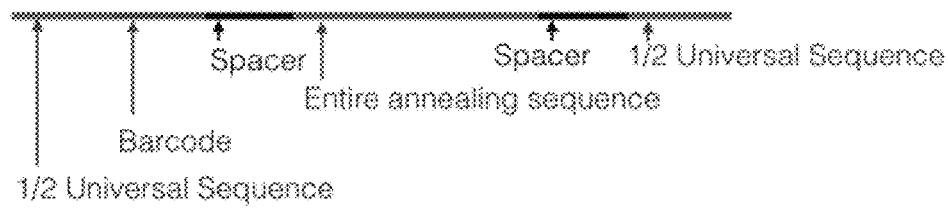
FIGS. 4A-E depict an exemplary probe design and maturation strategy for manufacture of padlock or gap-fill probes by oligonucleotide library synthesis, such as by DNA microarray, in accordance with embodiments.
Figure 4B:
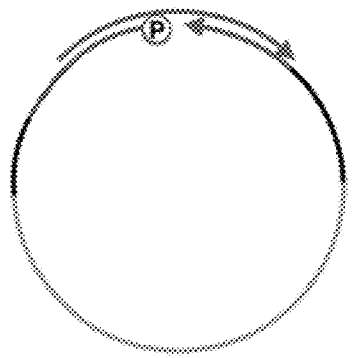
Figure 4C:
Figure 4D:
Figure 4E:
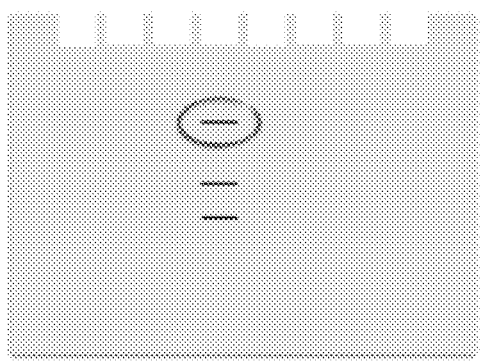

Additional probe design and maturation strategies are shown in FIGS. 4A-E. FIG. 4A-E depicts an exemplary probe design and maturation strategy for manufacture of padlock or gap-fill probes by oligonucleotide library synthesis, such as by DNA microarray. FIG. 4A shows a schematic of the probe design featuring conserved sequences on the ends, which may also be used for amplification of the nucleic acid material, such as by PCR or IVT. Alternatively, additional sequences 3' and 5' of the red domains may be included (not shown) for the purpose of amplification or sub-pool amplification. A barcode domain is included for the purpose of molecular identification. A central sequence is substantially complementary to the target sequence for the purpose of directing the probe to the target molecule via a nucleic acid hybridization reaction. FIG. 4B shows: 1) After amplification of the probe pool to sufficient quantity, a splint ligation reaction circularizes the probe. FIG. 4C shows: 2) Second-strand synthesis, such as by a non-displacing DNA polymerase, generates a second complementary strand featuring a nick at the 5' end of the second-strand synthesis primer. FIG. 4D shows: 3) A type IIS restriction enzyme is used to create a double-strand break within the targeting domain (annealing sequence). FIG. 4E shows: 4) The mature probe is isolated, such as by electrophoretic gel purification technique. This process may be referred to as probe maturation, encompassing the steps of amplification and processing required for converting an as-synthesized nucleic acid probe into a form suitable for use in assay.

Example 2—Validation of Microarray-Synthesized FISSEQ Primer Library

FIG. 2A illustrates an exemplary results of validation of microarray-synthesized FISSEQ primer library. FIG. 2A shows that the payload length of this library is distributed around 0, suggesting that the synthesis and/or amplification of the library filed. The target payload size is indicated by the dotted line. FIG. 2B shows that a significant fraction of the pool contains a payload that matches the expected size, which is indicated by the dotted line. Note there is also a significant fraction of payloads within a few bases in length, which reflects the main error mode of array synthesis—deletions. FIG. 2C shows violin plot of the distribution of payloads from FIG. 2B shows that most members of the library are present at an average of a few copies. Some members are missing from the final library, and also some members are present at ~10× the average level of the library.

Example 3—Targeted FISSEQ Capture Schemes

Figure 3A:
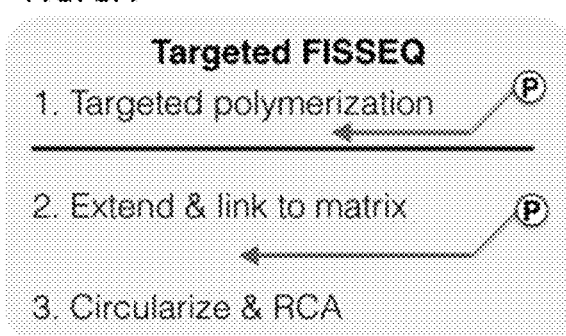
FIGS. 3A-F depict exemplary targeted FISSEQ capture schemes, in accordance with embodiments.
Figure 3B:
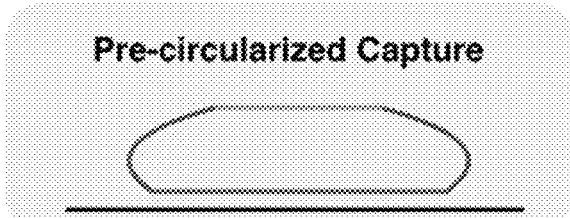
Figure 3C:
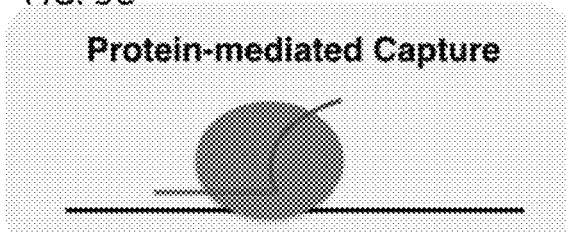
Figure 3D:
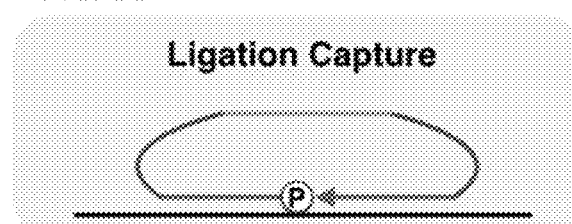
Figure 3E:
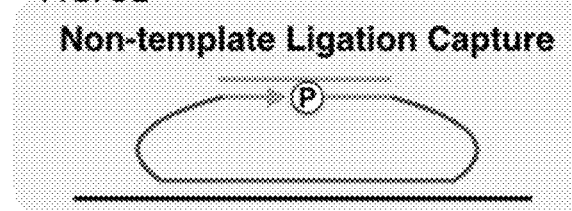
Figure 3F:
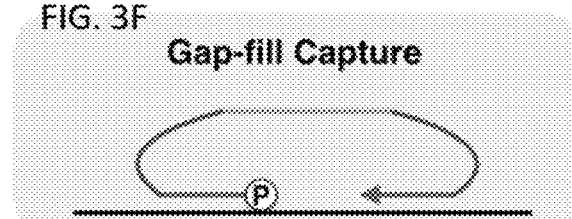

FIGS. 3A-F depict exemplary targeted FISSEQ capture schemes. As shown in FIG. 3, the FISSEQ capture probe can be used to capture target nucleic acid molecule region, such as a RNA, mRNA, DNA, or genomic locus. The capture probe comprises the sequence domain substantially complementary to the target molecule sequence and a non complementary tail region containing adaptor sequences, sequencing primer domains, and barcode sequence domains. FIG. 3A shows a targeted polymerization reaction is directed to the target molecule via the targeting sequence domain, which serves to prime a nucleic acid polymerization reaction, such as reverse transcription of RNA into cDNA, or second-strand synthesis of a DNA sequence by a DNA polymerase. The primer is extended by the polymerase, incorporating endogenous sequence, and linked into the FISSEQ 3D hydrogel matrix to preserve the spatial localization of the molecule. Finally, the template is circularized and amplified, such as by rolling circle amplification, for detection via sequencing. FIG. 3B shows a pre-circularized probe is hybridized against a target molecule and subsequently amplified, such as by rolling circle amplification, for detection via sequencing. FIG. 3C shows a protein and nucleic acid capture probe complex is used to mediate selection of the target molecule, for the purpose of directing FISSEQ library construction biochemistry to the target molecule. Library construction biochemistry may include, but is not limited to, cutting, ligating, and other nucleic acid reactions for the purpose of sequencing, or association of a cognate barcode or otherwise detectable label. FIG. 3D shows a "padlock probe" is designed such that the ends of the probe come into immediate contact when hybridized to the target molecule. A ligase reaction forms the phosphodiester bond circularizing the probe. Finally, the template is circularized and amplified, such as by rolling circle amplification, for detection via sequencing. FIG. 3E shows a probe is hybridized to the target molecule via the complementarity domain, with a subsequent non-target-molecule-dependent ligation reaction serving to circularize the probe, followed by amplification and sequencing. FIG. 3F shows a "gap fill" probe (also commonly referred to as a molecular inversion probe, or MIP) is used for targeted FISSEQ. The hybridization arms of the probe anneal to the target molecule forming a gap between the 3' and 5' ends. Subsequently, a nucleic acid polymerization reaction primed by the 3' end of the probe serves to extend the probe incorporating endogenous sequence-templated bases. Subsequently, a ligase forms a phosphodiester bond circularizing the probe. Finally, the template is circularized and amplified, such as by rolling circle amplification, for detection via sequencing.

Example 4—Targeted FISSEG of OncoType Dx Panel

Figure 5:
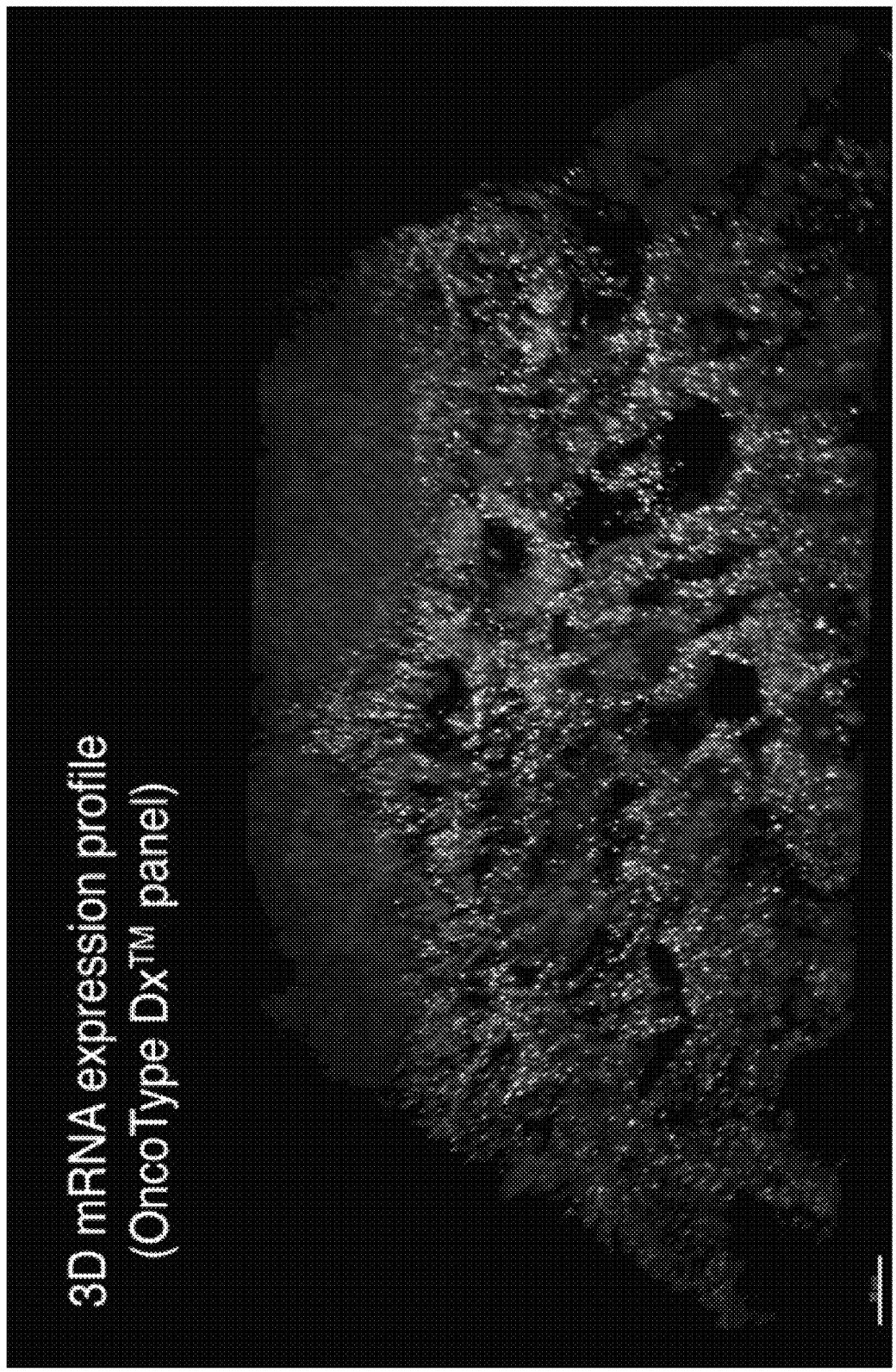
FIG. 5 illustrates an exemplary image of targeted FISSEQ of human breast cancer tissue biopsy sample, in accordance with embodiments.
Figure 6:
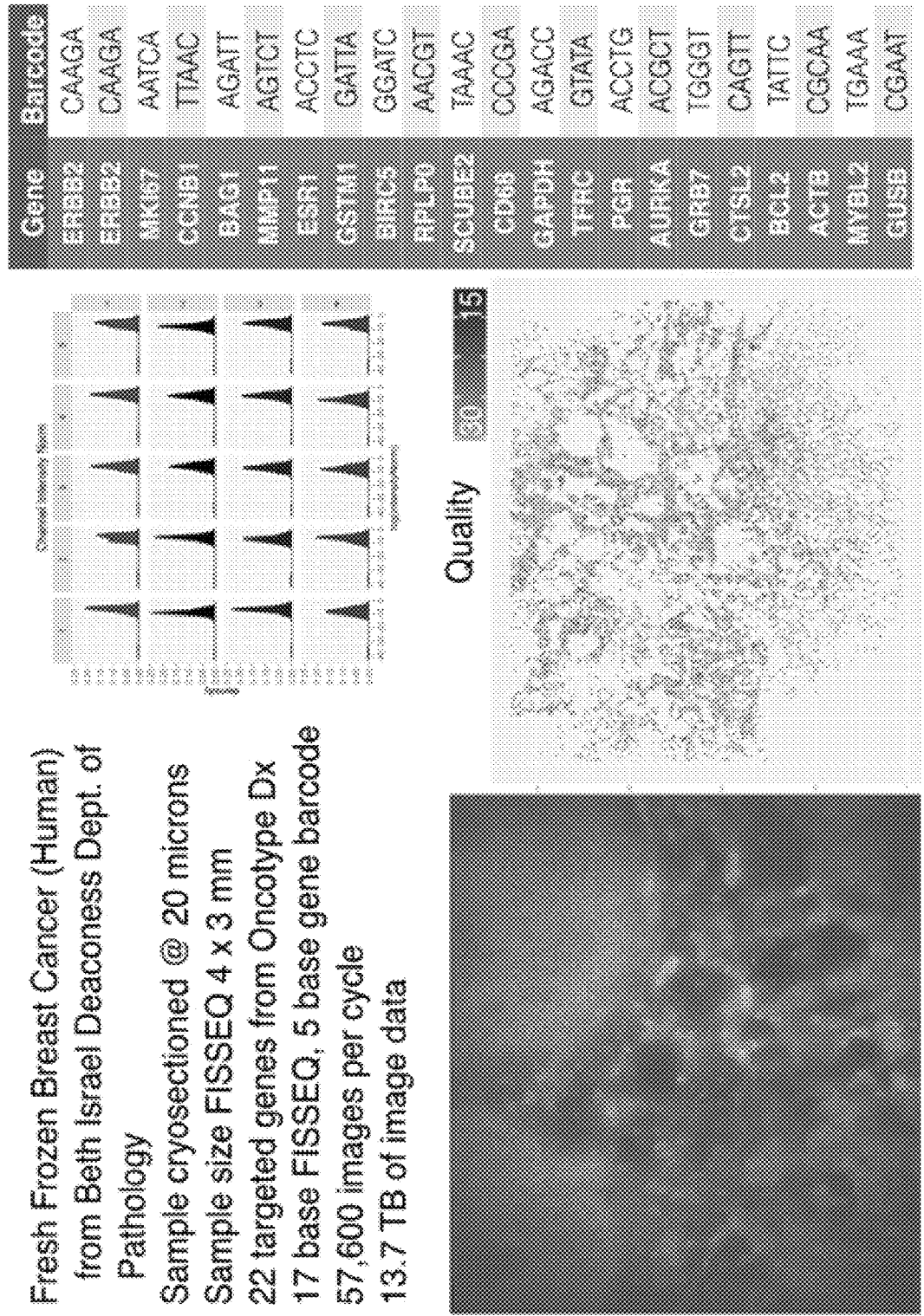
FIG. 6 illustrates exemplary experimental data summary of sequencing from FIG. 5, in accordance with embodiments.

OncoType Dx gene panel was used as an example to demonstrate the workflow of targeted FISSEQ. FIG. 5 depicts an exemplary image of targeted FISSEQ of human breast cancer tissue biopsy sample. A pool of targeted reverse transcription primers initiate reverse transcription reaction at genes of the clinically-relevant OncoType Dx gene panel. The image depicts a single base of sequencing reaction, rotated in 3D to demonstrate molecular identification within the 3D FISSEQ hydrogel and original tissue sample. Gene expression profiles of the OncoType Dx genes are computed. FIG. 6 shows exemplary experimental data summary of sequencing from FIG. 5. Upper text includes relevant experimental data. Lower left panel shows the location of molecular identification events superimposed over the tissue image. Lower middle panel shows the same molecules indicating a sequencing quality metric. Upper middle graphs show the distribution of sequencing signals for each base over the barcode sequence, demonstrating high quality sequencing data. Right table shows the genes included in the assay and associated sequence barcodes.

ing; a polyacrylic acid; a polyvinylsulfonic acid; or an alginate; and wherein said cell is integrated with a hydrogel matrix; and (b) subjecting said reaction mixture to conditions sufficient to conduct said hybridization reaction between said target nucleic acid molecule and said probe having sequence complementarity with said target sequence of said target nucleic acid molecule, wherein during said hybridization reaction, said hybridization reaction enhancing agent facilitates said hybridization reaction between said target nucleic acid molecule and said probe having sequence complementarity with said target sequence of said target molecule; and (c) subjecting said functional group to conditions sufficient to inactivate said hybridization reaction enhancing agent.

2. The method of claim 1, further comprising inactivating said hybridization reaction enhancing agent.

3. The method of claim 2, wherein inactivating said hybridization reaction enhancing agent comprises inactivating said functional group by rendering an ionic group of said functional group to have a neutral charge, or by reducing hydration functionality of a hydrating group of said functional group.

4. The method of claim 1, further comprising, subsequent to (b), conducting an enzymatic reaction.

5. The method of claim 4, wherein said enzymatic reaction comprises reverse transcription, ligation, or nucleic acid polymerization.

6. The method of claim 4, wherein said hybridization reaction enhancing agent enhances a rate of said enzymatic reaction.

What is claimed is:

1. A method for enhancing a hybridization reaction in a cell, comprising:
    (a) providing said cell and a reaction mixture, said reaction mixture comprising (i) a target nucleic acid molecule, (ii) a probe having sequence complementarity with a target sequence of said target nucleic acid molecule, and (iii) a hybridization reaction enhancing agent comprising a polymer backbone, wherein said hybridization reaction enhancing agent enhances a rate of a hybridization reaction between said target nucleic acid molecule and said probe having sequence complementarity with said target sequence of said target molecule, wherein said hybridization reaction enhancing agent comprises a functional group that facilitates inactivation of said hybridization reaction enhancing agent, wherein said hybridization reaction enhancing agent comprises a modified polyethylene glycol (PEG) comprising an ionic PEG, a cleavable PEG or a hydrat- 7. The method of claim 1, wherein said functional group is a hydrating group.

8. The method of claim 7, wherein said hybridization reaction enhancing agent comprises a cleavable linker between said polymer backbone and said hydrating group.

9. The method of claim 1, wherein said functional group is cleavable.

10. The method of claim 9, further comprising cleaving said functional group.

11. The method of claim 10, further comprising washing said functional group away from said target nucleic acid molecule.

12. The method of claim 11, further comprising conducting an enzymatic reaction subsequent to cleaving said functional group.

13. The method of claim 11, wherein said enzymatic reaction comprises reverse transcription, ligation, or nucleic acid polymerization.

14. The method of claim 1, further comprising, prior to (b), generating said hydrogel matrix in said cell.

15. The method of claim 1, wherein said reaction mixture further comprises a buffer.

16. The method of claim 15, wherein said buffer comprises a blocking agent, which blocking agent impedes non-specific binding of probes to off-target sequences of said target nucleic acid molecule.

17. The method of claim 1, wherein said polymer backbone is an ionic polymer backbone.

18. The method of claim 17, wherein said hybridization enhancing agent comprises a polyionic, polyelectrolyte, hydrophilic, or hydrating polymer.

* * * * *

SEQUENCE LISTING

```
<160> NUMBER OF SEQ ID NOS: 1

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acttcagctg ccccgggtga aga                                             23
```